(12) United States Patent
Fisher

(10) Patent No.: US 6,264,672 B1
(45) Date of Patent: Jul. 24, 2001

(54) EMBOLI CAPTURING DEVICE

(75) Inventor: John S. Fisher, Belleair, FL (US)

(73) Assignee: Biopsy Sciences, LLC, Clearwater, FL (US)

( * ) Notice: Subject to any disclaimer, the term of this patent is extended or adjusted under 35 U.S.C. 154(b) by 0 days.

(21) Appl. No.: 09/426,438

(22) Filed: Oct. 25, 1999

(51) Int. Cl.[7] ................................................. A62M 29/00

(52) U.S. Cl. ...................... 606/200; 606/200; 606/194; 606/159

(58) Field of Search ................................. 604/101, 105, 604/104, 194, 500; 128/344, 898; 600/3; 606/194, 200, 159, 198, 181

(56) References Cited

U.S. PATENT DOCUMENTS

| | | | |
|---|---|---|---|
| 4,723,549 | * | 2/1988 | Wholey et al. . |
| 6,146,416 | * | 11/2000 | Andersen . |
| 6,152,947 | * | 11/2000 | Ambrisco et al. . |
| 6,152,956 | * | 11/2000 | Pierce . |

\* cited by examiner

Primary Examiner—Richard K. Seidel
Assistant Examiner—Kevin C. Sirmons
(74) Attorney, Agent, or Firm—Ronald E. Smith; Smith & Hoper, P. A.

(57) ABSTRACT

An apparatus used in balloon angioplasty and/or stenting in a first embodiment includes a guide wire, a balloon catheter that ensleeves the guide wire, and a guide catheter that ensleeves the balloon catheter. The balloon catheter has a plurality of longitudinally-extending, circumferentially spaced apart slots formed in it to define a plurality of elongate members between the slots. A joint is formed at the proximal, distal, and mid-point of each elongate member. Displacing the respective proximal and distal joints toward one another causes the respective middle joints to displace radially outwardly, and radial inward travel of the middle joints is caused by increasing the distance between the proximal and distal joints. A bead is formed in the distal end of the guide wire and retraction of the guide wire causes the bead to abut the distal end of the balloon catheter and displace it in a distal-to-proximal direction, opening the elongate, jointed members. A mesh that captures emboli while allowing blood perfusion partially overlies the jointed members and is opened when the jointed members are opened and closed when they are closed. The guide catheter is used to close the jointed members and the emboli-capturing mesh at the conclusion of the angioplasty procedure. In a second embodiment, the jointed members are formed in an inner lumen received with a delivery catheter. In a variation of the second embodiment, a predetermined extent of the inner lumen is enlarged to facilitate the formation of the jointed members. In a third embodiment, a guide wire having an outer coil and an inner rod that is slideably received within it is modified so that the jointed members are formed in the outer coil and the mesh is opened and closed by axially retracting and advancing the inner rod with respect to the outer coil, respectively.

5 Claims, 26 Drawing Sheets

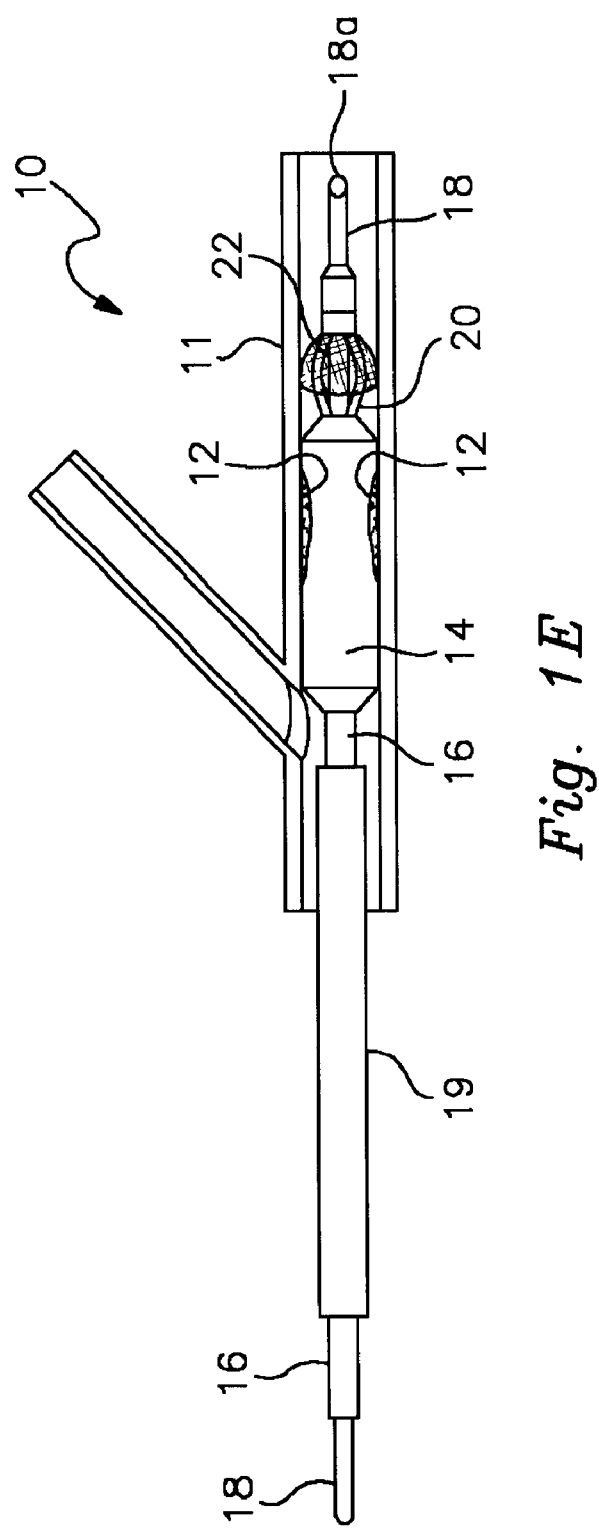

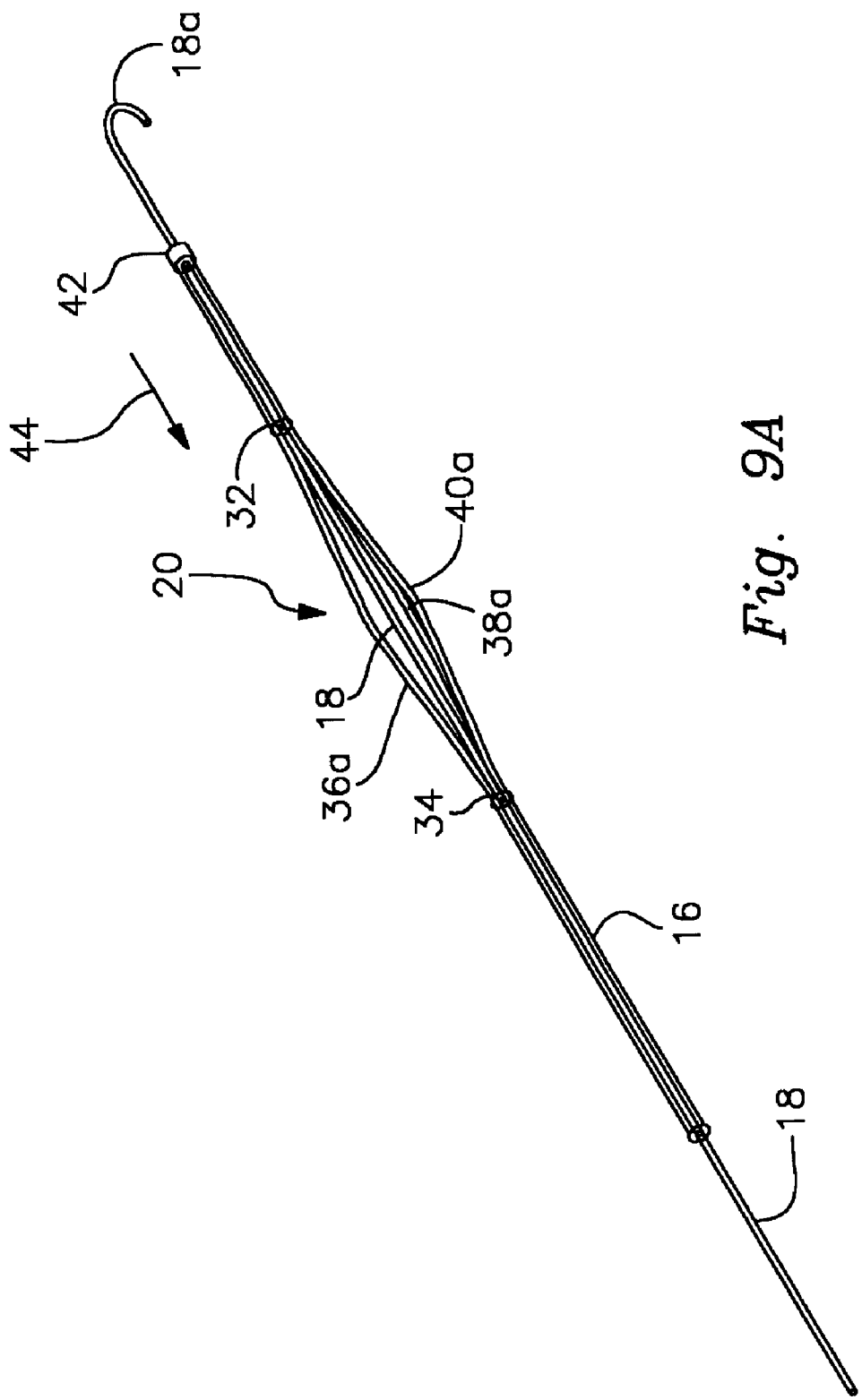

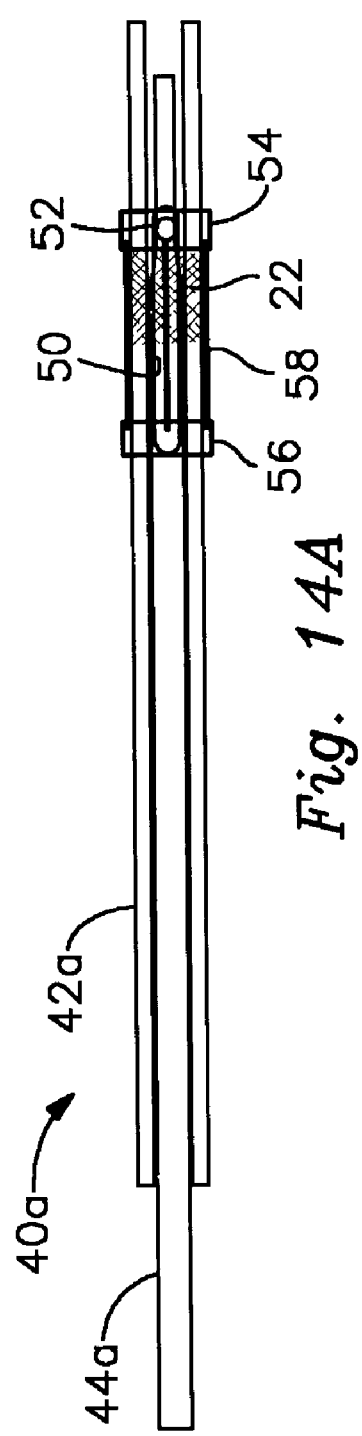
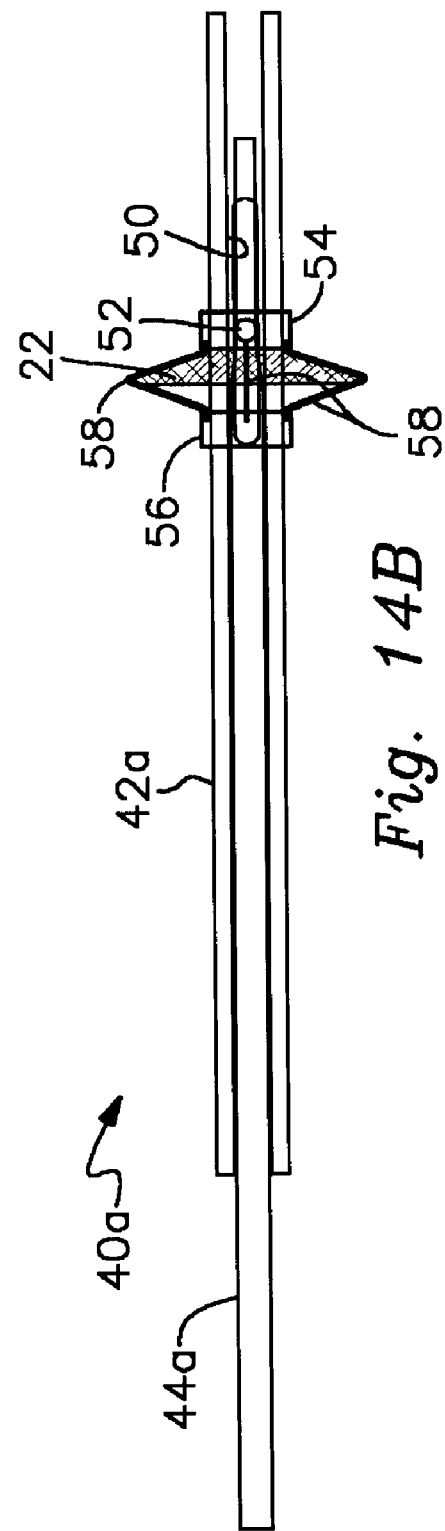
Fig. 14A
Fig. 14B

EMBOLI CAPTURING DEVICE

BACKGROUND OF THE INVENTION

1. Field of the Invention

This invention relates, generally, to endovascular surgical tools. More particularly, it relates to a tool used in balloon angioplasty and stenting of blood vessel narrowings (stenoses).

2. Description of the Prior Art

Percutaneous angioplasty is an efficacious treatment for improving the blood carrying capacity of an artery that has become occluded by plaque, calcification, and other deposits. There are several ways of performing the procedure and the type and number of catheters and other tools used may vary between differing procedures. Typically, a needle puncture is made into an artery and an elongate guide wire is fed through the puncture site until it has traversed the stenotic lesion (the are where the plaque has built up). A guide catheter having a relatively large diameter is then introduced into the artery, using the guide wire to guide it. A balloon-carrying catheter is then fed through the guide catheter, also using the guide wire as a guide. The guide catheter is then advanced to a preselected point so that its distal end is downstream of the stenotic lesion, and the balloon catheter is positioned so that the balloon is in registration with said lesion, also known as a stenosis. The guide catheter is withdrawn a relatively short distance to expose the balloon catheter. The balloon is then inflated to permanently dilate and tear the two inner layers of the artery, thereby enlarging its diameter, breaking up the stenosis, thereby increasing the blood-carrying capacity of the artery. An expandable stent may be carried on the outer surface of the balloon and left in place after the balloon is deflated and withdrawn. Alternatively, a self-expanding stent may be deployed over the treated lesion using a different delivery catheter. The stent holds the arterial walls in their expanded condition. After the balloon is deflated, the balloon catheter is withdrawn into the guide catheter, and both of said catheters and the guide wire are withdrawn to conclude the procedure.

The primary drawback to balloon angioplasty or stenting is the creation of debris and thrombus that can clog blood vessels downstream of the treatment site. The stretching of the two inner arterial walls breaks up the stenotic lesion and creates debris known as emboli. Accordingly, when the balloon is deflated, the emboli flow downstream with the blood. If the stenotic lesion is in the iliac or femoral arteries, the emboli may flow to the feet; this may or may not be problematic. However, if the stenotic lesion is in the carotid artery, the emboli can flow into various brain vessels and cause permanent brain damage. Similarly, kidney damage can ensue from dilating a lesion in the main renal artery. For this reason, balloon angioplasty carries a high risk of embolic complications for stenotic lesions in the carotid, renal, and coronary arteries unless means are provided for preventing the flow of emboli to the blood vessels of the brain, kidney, or heart, respectively.

U.S. Pat. No. 5,833,644 discloses a complex catheter system that deploys at least two additional balloons that flank the main balloon that stretches the blood vessel. When inflated, the auxiliary balloons isolate the treatment area so that emboli cannot flow therefrom. However, no blood can flow to the brain when the auxiliary balloons are inflated, so the physician must perform the treatment in an expedited manner to avoid brain damage arising from oxygen deprivation. This can result in less than optimal treatment. Catheters of this type also include dedicated lumens for aspiration and irrigation and may require a complex electromechanical system to operate and control the saline flow rate, pressure, and the like.

PCT patent application No. PCT/US98/01894 filed by Yadav, published Aug. 6, 1998, discloses an emboli-catching device that is mounted to the distal end of a guidewire. It is positioned downstream of the stenotic lesion and opened up, much like an umbrella, to catch the emboli created by inflation of the angioplasty balloon. It is designed for use in the carotid artery and is formed of a material that is permeable to red blood cells so the brain is not deprived of oxygen during its deployment. However, since it must be positioned downstream of the stenotic lesion, it cannot be used in the lower half of the body because such use would require that it be fed to its operative location from a point in the upper half of the body. Moreover, the mechanism required to deploy and retract and emboli-catching means requires a dedicated sheath which makes the procedure relatively complex.

Several prior art emboli-catching devices also rely upon mesh-carrying frames that are formed of a flexible and resilient material such as a nickel-titanium alloy. The problem with such devices is that they pop open when they emerge from a containment catheter. Some of them spring open under their inherent bias until they hit the interior walls of an artery, and others spring open to a predetermined diameter that may be less than the diameter of an artery. In either case, the physician cannot instantaneously control the amount of opening or closing of the mesh. In other words, the nickel-titanium devices are either fully open or fully closed and the physician cannot open or close such devices to an infinite plurality of functional positions of adjustment because the opening or closing of the emboli-catching device is not under the positive control of the physician.

What is needed, then, is an emboli containment and removal device that does not block blood flow when in use, which can be used with any diagnosis or treatment catheter, which is small, which is mechanically simple in construction, and which is under the positive control of the physician. Moreover, such a device is needed that can be used in the carotid artery and in other blood vessels, including those in the region of the kidneys, heart, and peripheral blood vessels.

However, it was not obvious to those of ordinary skill in this art how the needed improvements could be provided, in view of the art considered as a whole at the time the present invention was made.

SUMMARY OF THE INVENTION

The long-standing but heretofore unfulfilled need for an innovation that overcomes the limitations of the prior art is now met by a new, useful, and nonobvious invention. A first embodiment of the novel apparatus for performing balloon angioplasty and/or stenting includes a guide wire of elongate, flexible construction and a balloon catheter that slideably receives the guide wire. A plurality of longitudinally disposed, circumferentially spaced apart jointed members is formed in the balloon catheter near a distal end thereof. Each joint member of the plurality of joint members has a proximal joint, a distal joint longitudinally spaced apart from the proximal joint, and a middle joint that is substantially half-way between the proximal and distal joints. The jointed members have a position of repose where no bends are formed in any of the joints and the jointed members are therefore substantially flush with the exterior cylindrical wall of the balloon catheter. Each middle joint is displaced radially outwardly, with respect to a longitudinal axis of the balloon catheter, when the distance between its associated proximal and distal joints is reduced, and each middle joint is displaced radially inwardly when that distance is increased. A first displacement means is provided for selectively displacing each of the distal joints toward their associated proximal joints, and a second displacement means is provided for displacing each of the distal joints away from their associated proximal joints to return the jointed members to their position of repose. Both displacement means are under the positive control of a physician and the amount of displacement can be any amount so that the joint members have an infinite number of positions of functional adjustment.

A mesh structure of flexible construction has a generally frusto-conical configuration when in repose and is disposed in partially ensleeving relation to the balloon catheter. More particularly, in a first configuration, a first relatively short distal extent of the mesh structure is secured to the balloon catheter distally of the jointed members and a second predetermined proximal extent of the mesh structure ensleeves about half the extent of the jointed members. Thus, the proximal end of the mesh structure is enlarged in diameter when the middle joints are displaced radially outwardly. However, as will become clear as this disclosure continues, the just-described configuration of the mesh structure may be reversed so that the proximal end of the mesh structure is secured to the balloon catheter, proximally of the jointed members, and the distal end thereof is disposed in partially ensleeving relation to the jointed members so that the distal end of the mesh structure is enlarged when the middle joints are displaced radially outwardly. This enables the novel structure to be positioned downstream of a stenosis whether it is positioned in an artery where blood is flowing upwardly or downwardly with respect to the heart.

The mesh structure allows blood to flow therethrough and captures and retains emboli produced by a balloon angioplasty and/or stenting procedure when the middle joints are displaced radially outwardly. The mesh structure returns to its position of repose when the middle joints are displaced radially inwardly.

Significantly, the jointed members do not deploy automatically under the influence of shape memory when released from the confines of the guide catheter or other catheter which contains them; the deployment is under the control of a physician. Similarly, the return to said position of repose is not a result of the resiliency of the materials of which the balloon and/or stenting catheter and jointed members are made. Instead, the above-mentioned second displacement means is a guide catheter that is displaced by a physician in a proximal-to-distal direction to cause the collapse of the jointed members, it being understood that said guide catheter ensleeves the balloon and/or stenting catheter.

A nickel-titanium alloy is the preferred material of which the jointed members are made. Such an alloy is a shape memory alloy, but the memory is insufficient to cause full deployment of the mesh structure when the guide catheter is withdrawn in a distal-to-proximal direction to expose the balloon and the jointed members. Moreover, by employing the first and second displacement means, both of which are under the positive control of a physician, as the positive means for opening and closing said jointed members, respectively, there is no need for use an enhanced shape memory alloy such as a stress-induced martensite alloy as disclosed and broadly claimed in U.S. Pat. No. 5,067,957. Such shape memory alloys are not under the positive control of a physician in that they spring open to their maximum diameter when released from a containment catheter and thus cannot fulfill an important object of this invention.

The first displacement means is advantageously provided in the form of a stop means carried by the guide wire near a distal end thereof. The stop means has a breadth greater than the interior diameter of the balloon catheter. Accordingly, an initial displacement of the guide wire in a distal-to-proximal direction, by a physician, causes the stop means to abut a distal end of the balloon catheter and continued displacement causes the middle joints to displace radially outwardly. This enables the physician to open the jointed members to any percentage of full opening as may be desired.

The stop means is preferably provided in the form of a bead that is formed on the guide wire near its distal end. The bead has a diameter greater than the internal diameter of the balloon catheter; preferably, the bead diameter is greater than the internal diameter of the distal tip of said balloon catheter.

The mesh structure has a generally frusto-conical shape when the middle joint members are radially deployed. A first end of the mesh structure has a first diameter, a second end has a diameter greater than the first diameter, and a generally conical body extends between the first and second ends. The diameter of the second end spans the lumen of the artery within which the novel balloon catheter is deployed so that all emboli produced by the treatment procedure are captured in the mesh.

In a second embodiment, the novel jointed members are formed in a catheter, sometimes known as an inner lumen, that is received within the balloon catheter. Due to the small diameter of the inner lumen, it may be enlarged in the region of the jointed members to facilitate their construction. However, if the inner lumen is formed of a suitable material, the enlarged part is not needed.

In a third embodiment, the novel jointed members are formed in a guidewire of the type having a coiled outer sheath and an elongate rod slideably mounted therein. The opening and closing of the jointed members is under the positive control of a physician because the physician controls the instantaneous position of the elongate rod.

It is a primary object of this invention to provide an emboli collector suitable for use in any part of the body, whether in a region where blood flows upwardly or downwardly with respect to the heart.

Another important object is to provide an emboli collector that is opened and closed by positive displacement means under the positive control of a physician so that said opening and closing is not dependent upon the use of special alloys having a shape memory.

Still another important object is to provide an emboli collector that may be formed in a balloon catheter, in an inner lumen, or in a guidewire.

Another object is to provide an emboli collector having a mechanically simple structure.

These and other important objects, features, and advantages of the invention will become apparent as this description proceeds.

The invention accordingly comprises the features of construction, combination of elements and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which:

FIG. 1E is a view like that of FIG. 1D, depicting an angioplasty balloon in its inflated configuration and the novel emboli collector in its open position;

FIG. 9A is a perspective view of the guide wire of FIG. 8 disposed in ensleeved relation to the novel balloon catheter when the jointed members of the novel frame are slightly deployed;

FIG. 14A is a longitudinal sectional view of a variation of the third embodiment when the jointed members are closed; and FIG. 14B is a view like that of FIG. 14A but with the jointed members deployed.

DETAILED DESCRIPTION OF THE PREFERRED EMBODIMENT

Figure 1A:
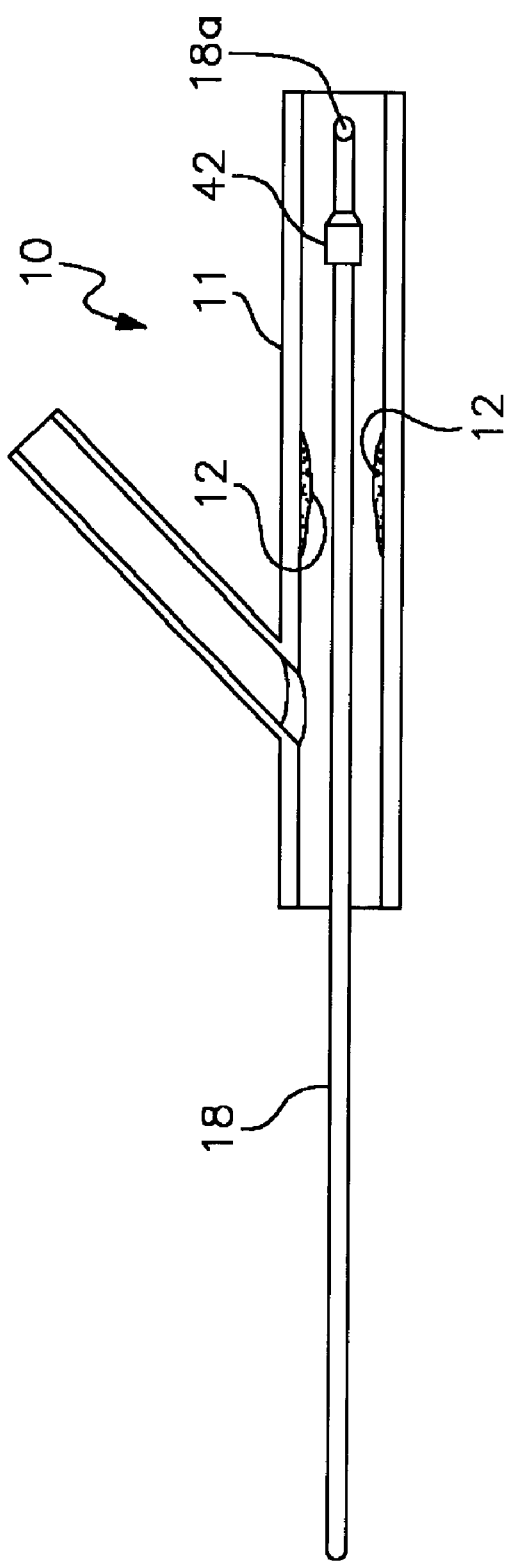
FIG. 1A is a longitudinal sectional view of a blood vessel and a guidewire inserted therewithin.

Referring now to FIGS. 1A–E and 2, it will there be seen that an exemplary embodiment of the invention is denoted as a whole by the reference numeral 10.

Artery 11 is partially occluded by plaque, calcification, and other debris 12 that builds up on the interior walls of the artery.

FIGS. 1A–E provide an animation that concludes with FIG. 1E where inflated balloon 14 is mounted about balloon catheter 16. Balloon catheter 16 ensleeves elongate guide wire 18. The distal end of guide wire 18 is denoted 18a.

Figure 1B:
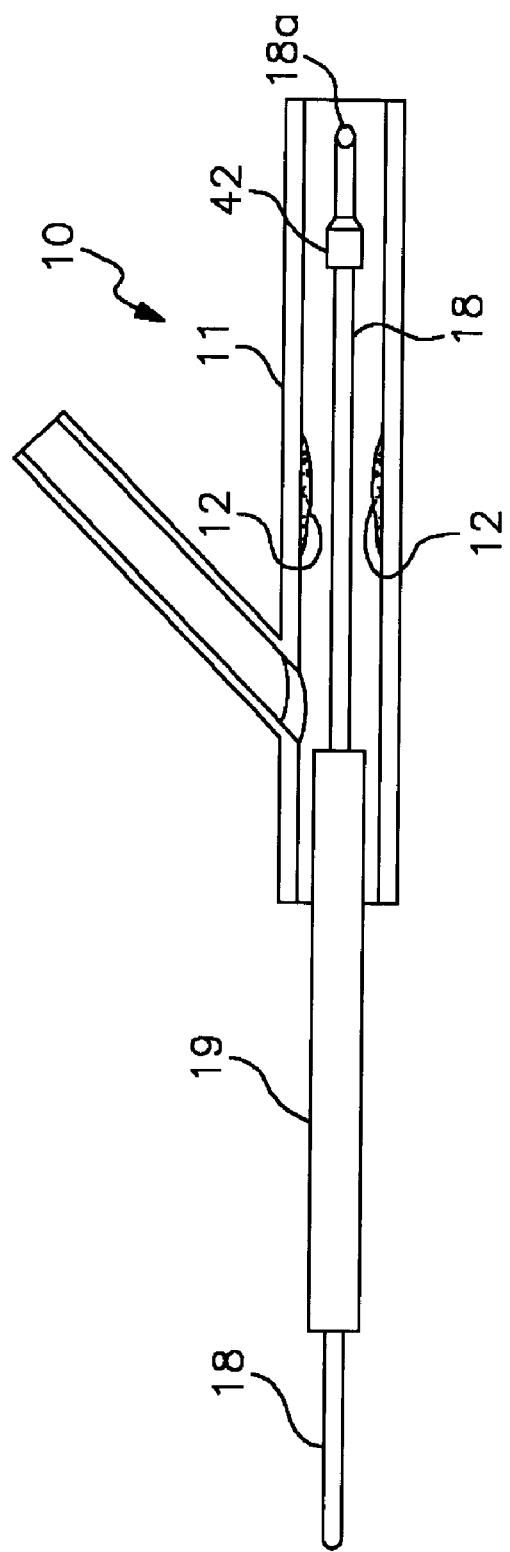
FIG. 1B is a view like that of FIG. 1A, depicting a guide catheter inserted over the guidewire.

In the first step of the novel procedure, depicted in FIG. 1A, elongate guidewire 18 is introduced into artery 11. A bead 42 or other enlargement is formed on said guidewire 18 near distal end or tip 18a. A guide catheter 19 is then introduced over guidewire 18, as depicted in FIG. 1B.

Figure 1C:
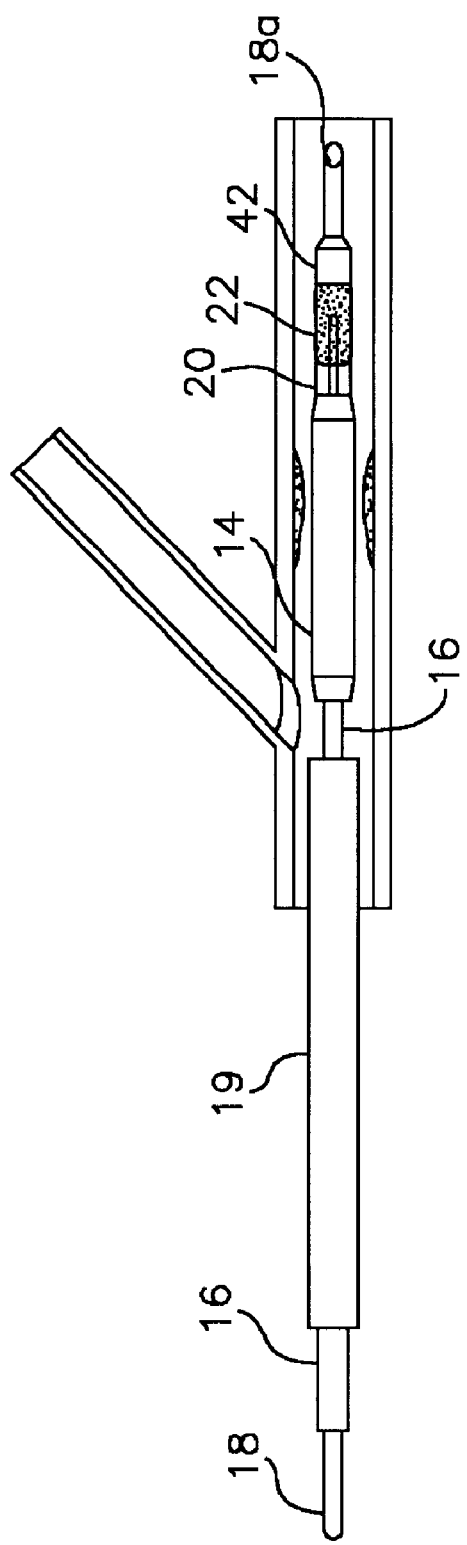
FIG. 1C is a view like that of FIG. 1B, further depicting a balloon catheter inserted over the guidewire and through the guide catheter.

Balloon catheter 16 is then introduced into guide catheter 19 as depicted in FIG. 1C, note that balloon 14 is in its deflated condition at this step of the procedure and that said balloon 14 must be positioned outside of guide catheter 16 before it can be inflated.

Figure 1D:
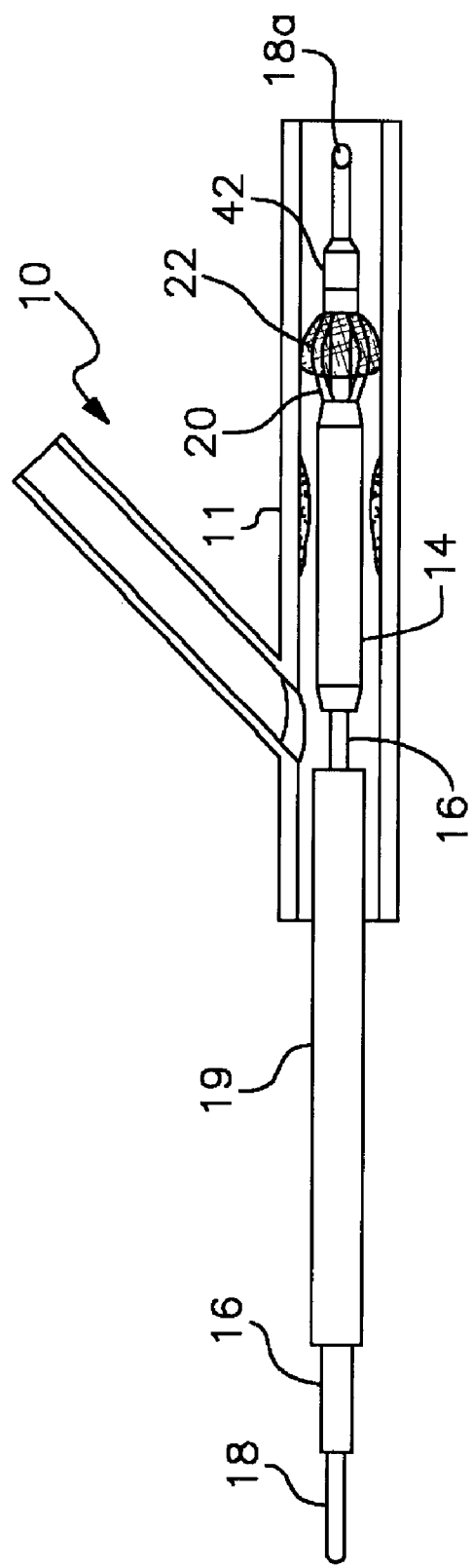
FIG. 1D is a view like that of FIG. 1C, depicting the novel jointed members in their deployed configuration.

A frame member 20 is formed integrally with balloon catheter 16 near the distal end thereof. A mesh structure 22 is depicted in its operable position in partial ensleeving relation to frame member 20. Said frame 20 and mesh 22 must also be positioned outside guide catheter 16 so that they may radially expanded in the manner hereinafter described. FIG. 1D depicts frame 20 when it has been opened by the physician. Note that balloon 14 is still not yet inflated.

Figure 2:
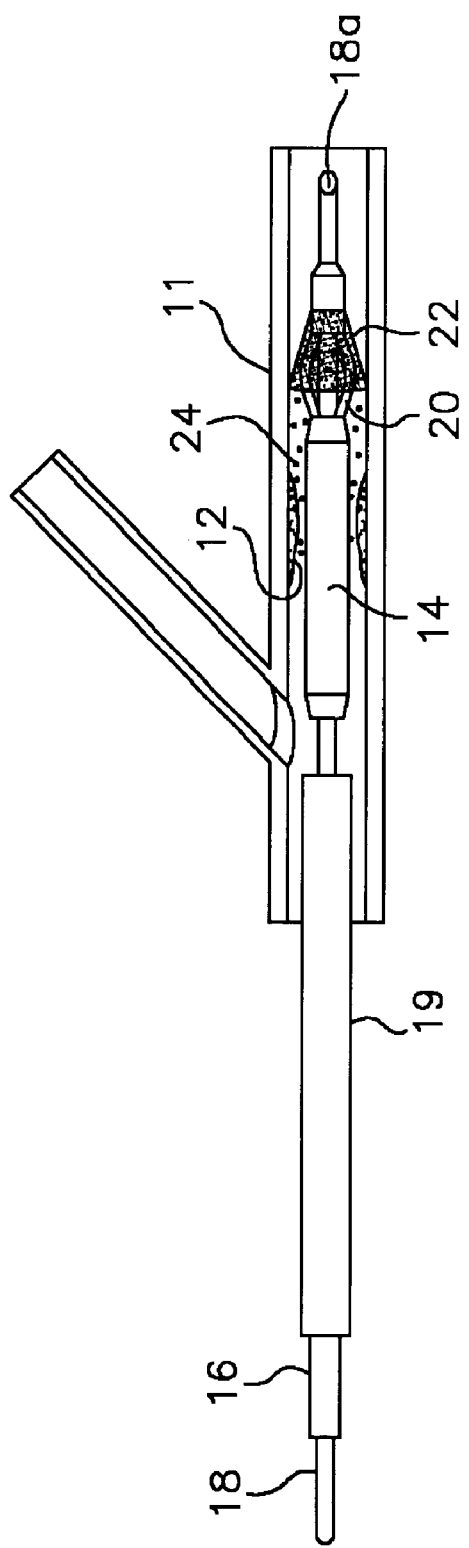
FIG. 2 is a view like that of FIG. 1E, depicting the flow of emboli into the novel emboli collector upon deflation of the balloon.

FIG. 1E depicts balloon 14 when inflated. When so inflated, it physically breaks up plaque 12 into small particles known as emboli. As depicted in FIG. 2, upon deflation of balloon 14, these small particles or emboli, denoted 24, are carried away by the bloodstream, thereby reducing the local occlusion.

Mesh structure 22 may be made of a molded polymer or a fabric such as Dacron® synthetic fabric, woven sufficiently tight to capture emboli 24 while allowing blood perfusion. Since emboli 24 are much larger in size than red blood cells, they are captured in mesh structure 22, and they remain captured therewithin when frame 20 is closed and balloon 14, balloon catheter 16, guide wire 18, guide catheter 19, frame 20 and mesh structure 22 are withdrawn from artery 10 at the conclusion of the angioplasty and/or stenting procedure.

Mesh 22 may be woven with a relatively tight mesh structure at its leading, open end, and with a looser mesh structure at its closed end. The transition between the tight structure and the looser structure would preferably be at a point about mid-length of the mesh structure. The looser mesh structure at the closed end would reduce back pressure and therefore direct blood flow toward the center of mesh 22 so that debris would be captured at the most distal end of mesh 22.

Figure 3:
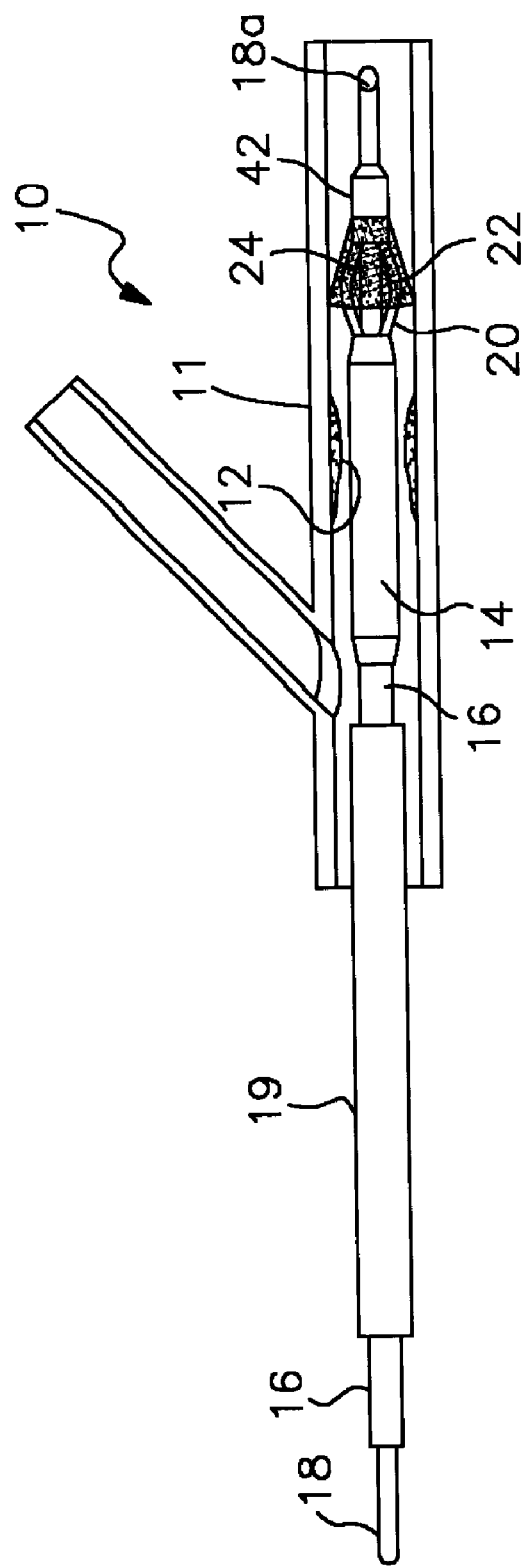
FIG. 3 is a view like that of FIG. 1E, depicting emboli collected in the novel emboli collector and depicting the balloon in its fully deflated configuration.

FIG. 3 depicts the novel assembly after balloon 14 has been fully deflated. Note that emboli 24 is captured within mesh structure 22.

Figure 4:
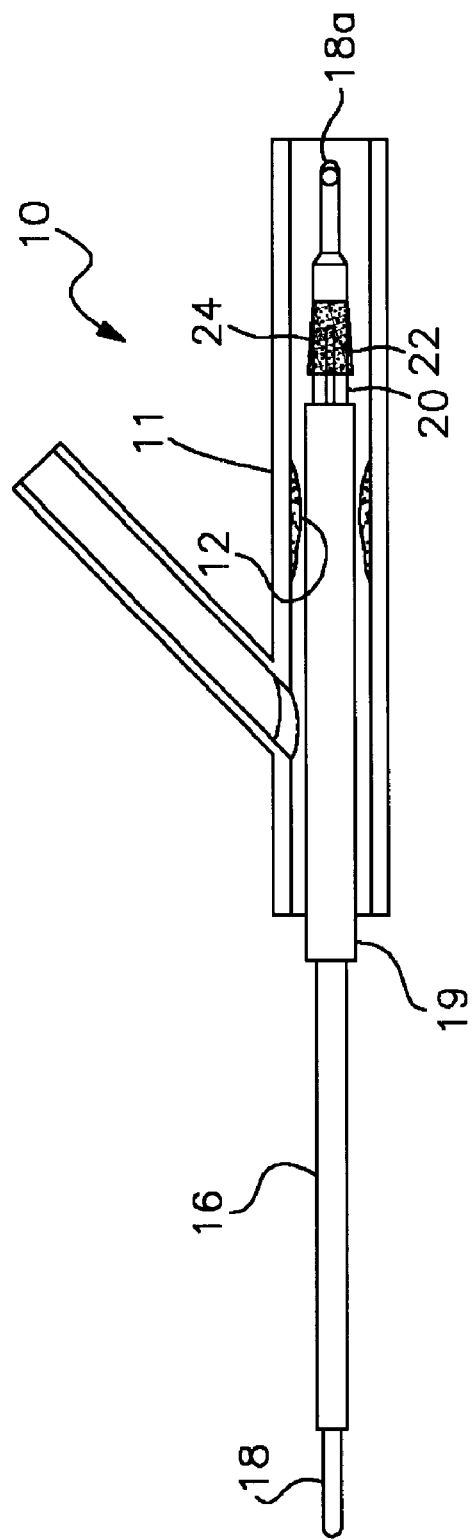
FIG. 4 is a view like that of FIG. 1E, depicting the guide catheter in an advanced position to ensleeve the deflated balloon of FIG. 3.

FIG. 4 depicts proximal-to-distal advancement of guide catheter 19 relative to balloon catheter 16. The distal or leading end of guide catheter 19 abuts the proximal or trailing end of frame 20.

Figure 5:
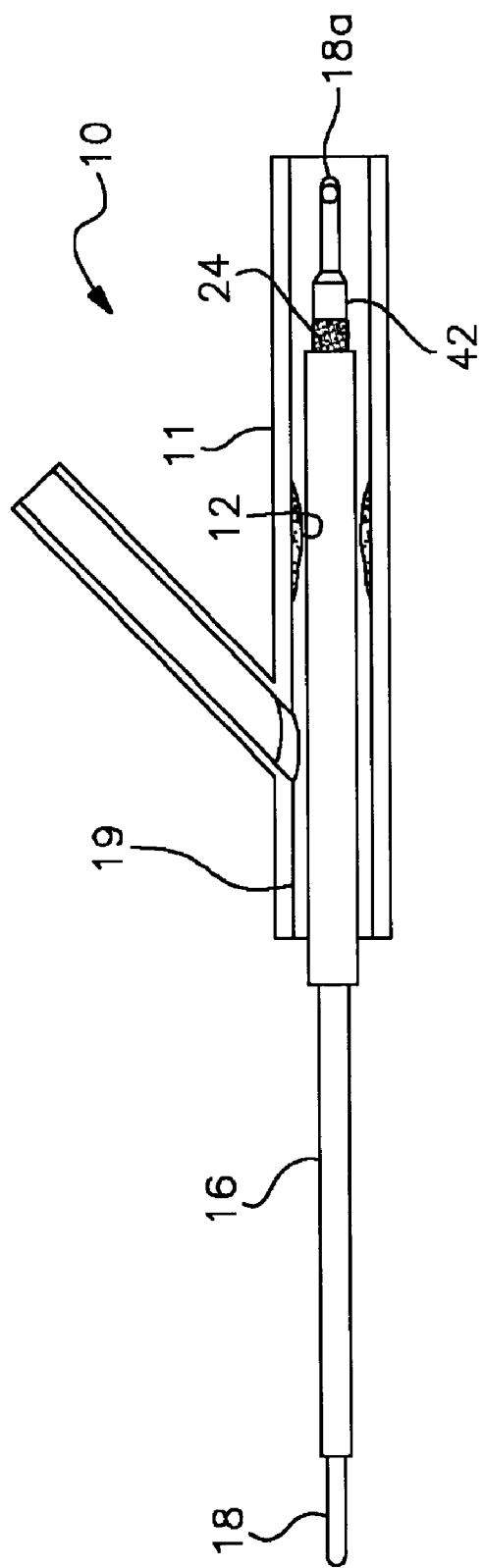
FIG. 5 is a view like that of FIG. 1E, depicting further proximal-to-distal displacement of the guide catheter or distal-to-proximal travel of the balloon catheter and hence retraction of the novel emboli collector into the guide catheter.

FIG. 5 depicts frame 20 as it is withdrawn into guide catheter 19. The relative proximal-to-distal travel of the guide catheter collapses frame 20 and causes it to close. Note how emboli 24 remain captured within mesh structure 22. By comparing FIGS. 4 and 5, it should be understood that guide catheter 19 is the positive displacement means for closing frame 20. Significantly, said positive displacement means is under the control of the physician.

Figure 6A:
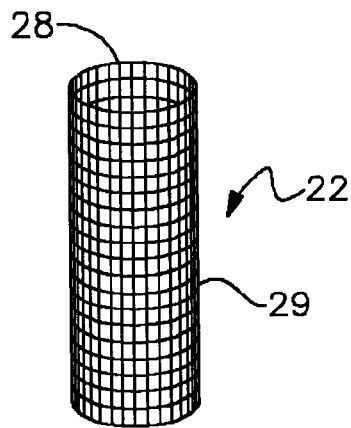
FIG. 6A is a perspective view of a first embodiment of the novel mesh structure when in repose.
Figure 6B:
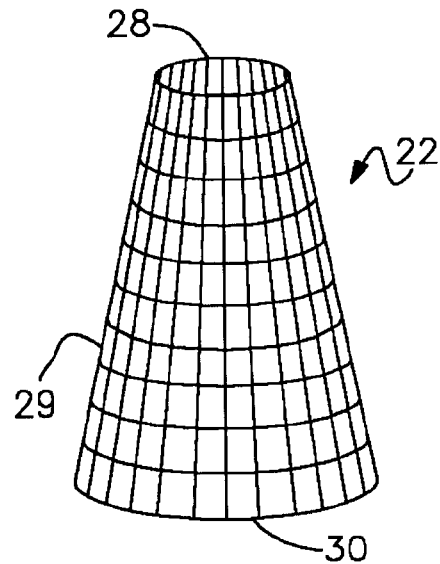
FIG. 6B is a perspective view of said first embodiment of the novel mesh structure when in an open configuration.
Figure 6C:
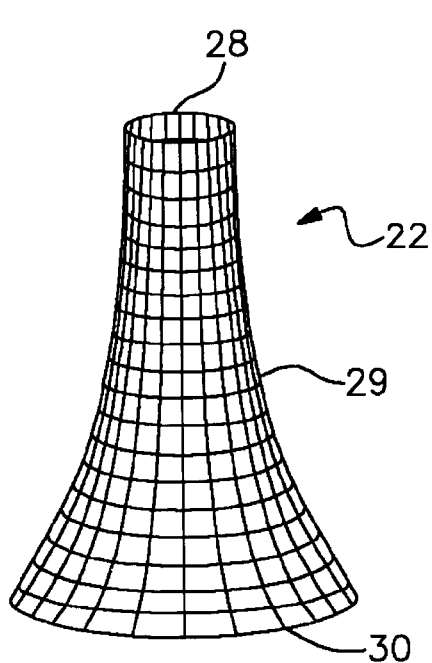
FIG. 6C is a perspective view of a second embodiment of the novel mesh structure when in its open configuration.
Figure 6D:
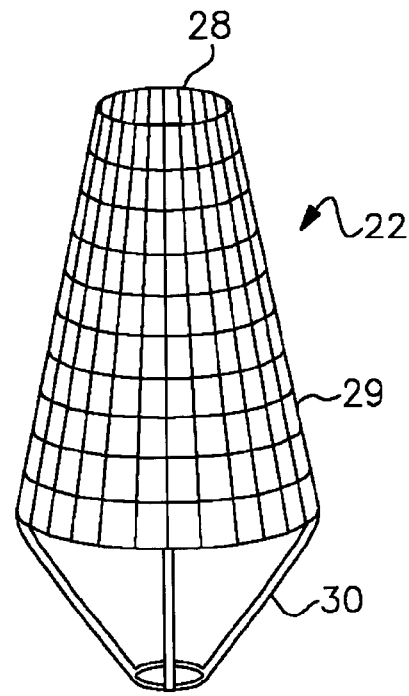
FIG. 6D is a perspective view of a third embodiment of the novel mesh structure when in its open configuration.

Mesh structure 22 may have a cylindrical construction when in repose, as depicted in FIG. 6A, a frusto-conical construction as depicted in FIG. 6B, a parabolic or hyperbolic form as depicted in FIG. 6C, or it may include extension arms for better attachment as depicted in FIG. 6D. The cylindrical configuration of 6A is not used if mesh structure 22 is not to be stretched.

The small diameter end 28 of mesh structure 22 is secured to balloon catheter 16 by a suitable adhesive or other attachment means. The main body 29 thereof at least partially overlies frame 20 so that opening frame 20 expands the large diameter end 30 thereof so that emboli is captured downstream of the stenotic lesion. When fully opened, large end 30 of mesh 22 should span the artery and conform to the circumference thereof so that no emboli can flow past said mesh 22.

Figure 7:
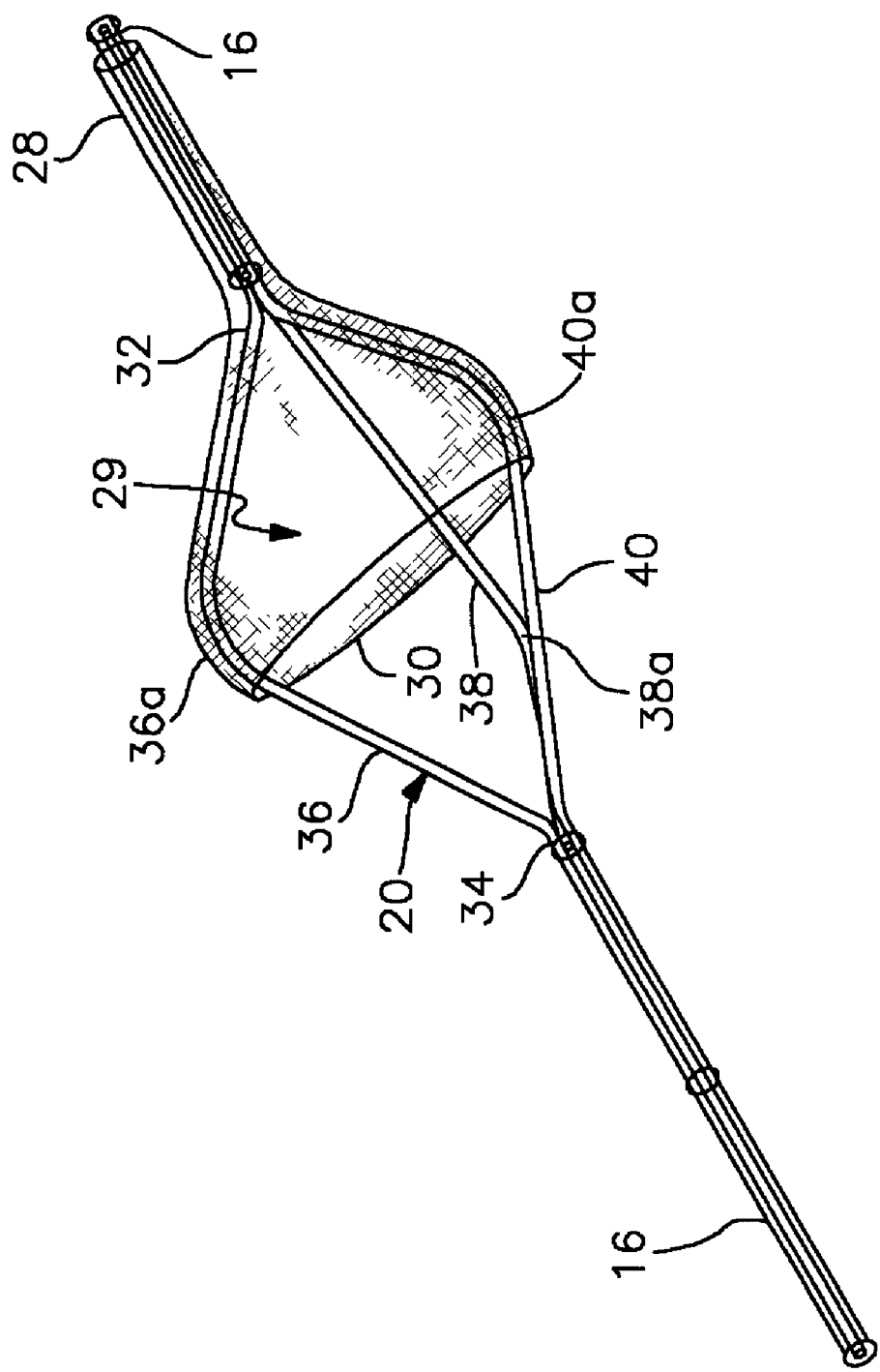
FIG. 7 is a perspective view depicting the novel mesh structure being held in an open configuration by the novel frame.

The structure of frame 20 and mesh 22 is perhaps better understood in connection with FIG. 7. Distal joint 32 and proximal joint 34 are formed in balloon catheter 16, and three (or more, not shown) elongate slots are formed therebetween to divide the part of balloon catheter 16 between said joints into three elongate sections 36, 38, and 40. Each of said sections is jointed mid-length thereof as at 36a, 38a, and 40a so that when the relative distance between distal and proximal joints 32 and 34 is decreased, said mid-length joints 36a, 38a, and 40a are displaced radially outwardly with respect to a longitudinal axis of balloon catheter 16 and when said relative distance is increased, said joints are displaced radially inwardly. Significantly, said decrease and increase in relative distance is under the positive control of the physician. Although jointed members 36, 38 and 40 are preferably formed of a nickel-titanium alloy, they do not rely upon shape memory for deployment or retraction. Instead, the physician controls the degree of deployment and contraction.

Again, note that the proximal end 30 of mesh 22 is secured to balloon catheter 16 and that main body 29 of said mesh is disposed at least in partial overlying relation to frame 20. Preferably, proximal end 30 extends slightly proximally of mid-length joints 36a, 38a, and 40a. This ensures substantially maximum opening of mesh 22 and hence maximum collection of emboli 24.

Figure 8:
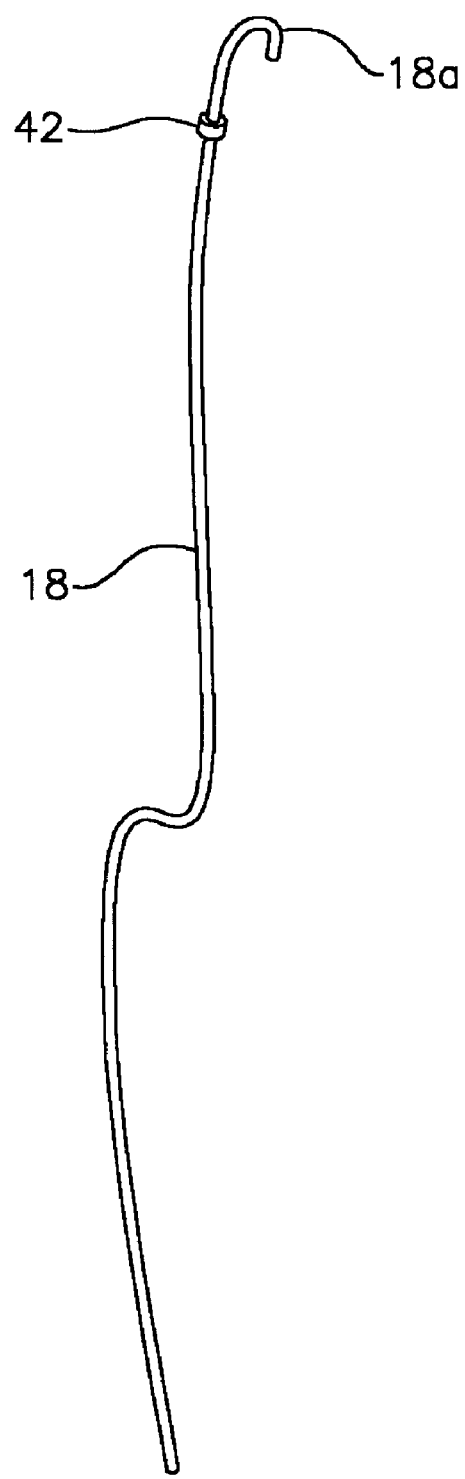
FIG. 8 is a perspective view of an elongate, flexible guidewire having a stop means formed thereon near a distal end thereof.
Figure 9B:
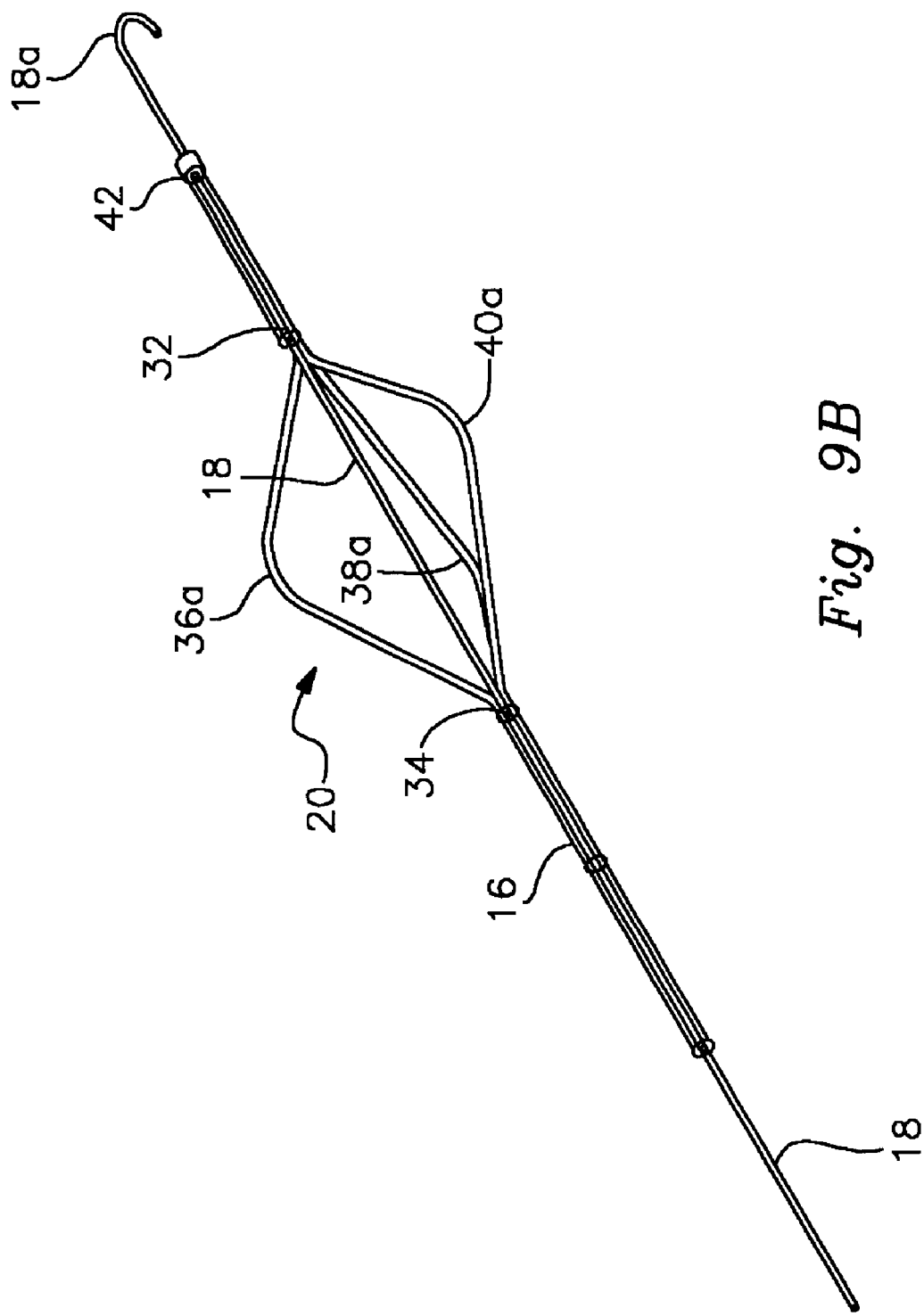
FIG. 9B is a perspective view like that of FIG. 9A when the jointed members are deployed to a greater extent.
Figure 9C:
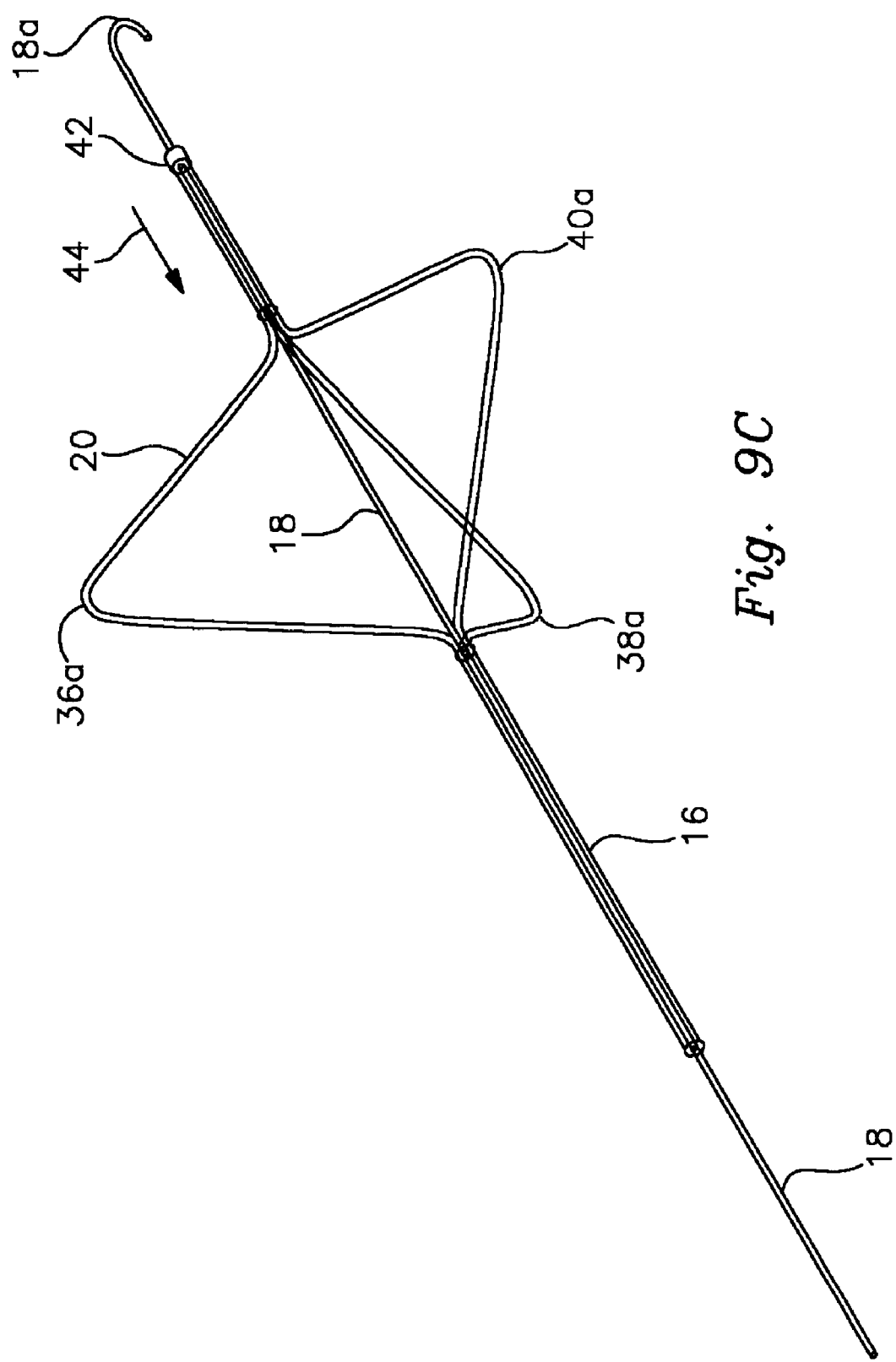
FIG. 9C is a perspective view like that of FIG. 9A when the jointed members are fully deployed.

There are several ways to accomplish the opening of frame 20 and hence of mesh 22. As depicted in FIG. 8, one way is to provide an enlargement, such as bead 42 near the distal end 18a of guide wire 18. As perhaps best understood in connection with FIGS. 9A, 9B, and 9C, bead 42 abuts against the distal end of balloon catheter 16 when guide wire 18 is pulled toward the physician, i.e., when guide wire 18 is displaced in a distal-to-proximal direction as indicated by single-headed directional arrow 44 in said Figures. The mesh structure is not depicted in these Figures to simplify them. Note that the distance between joints 32 and 34 decreases as said guide wire is pulled in the direction of arrow 44.

Figure 10A:
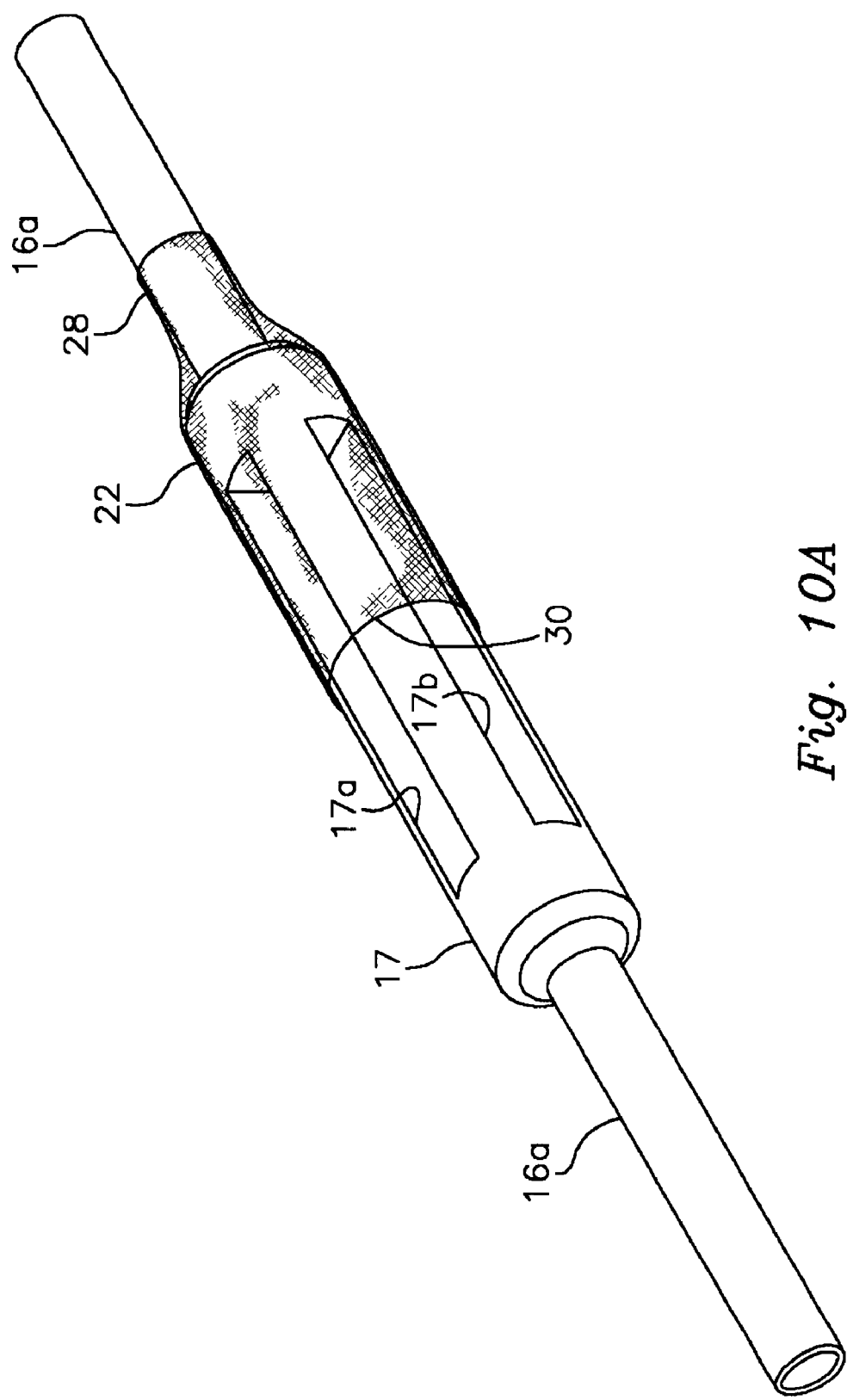
FIG. 10A is a perspective view of the second embodiment where an inner lumen received within a balloon delivery catheter is enlarged along a predetermined extent to facilitate the formation therein of an increased number of slots and hence an increased number of jointed members.
Figure 10B:
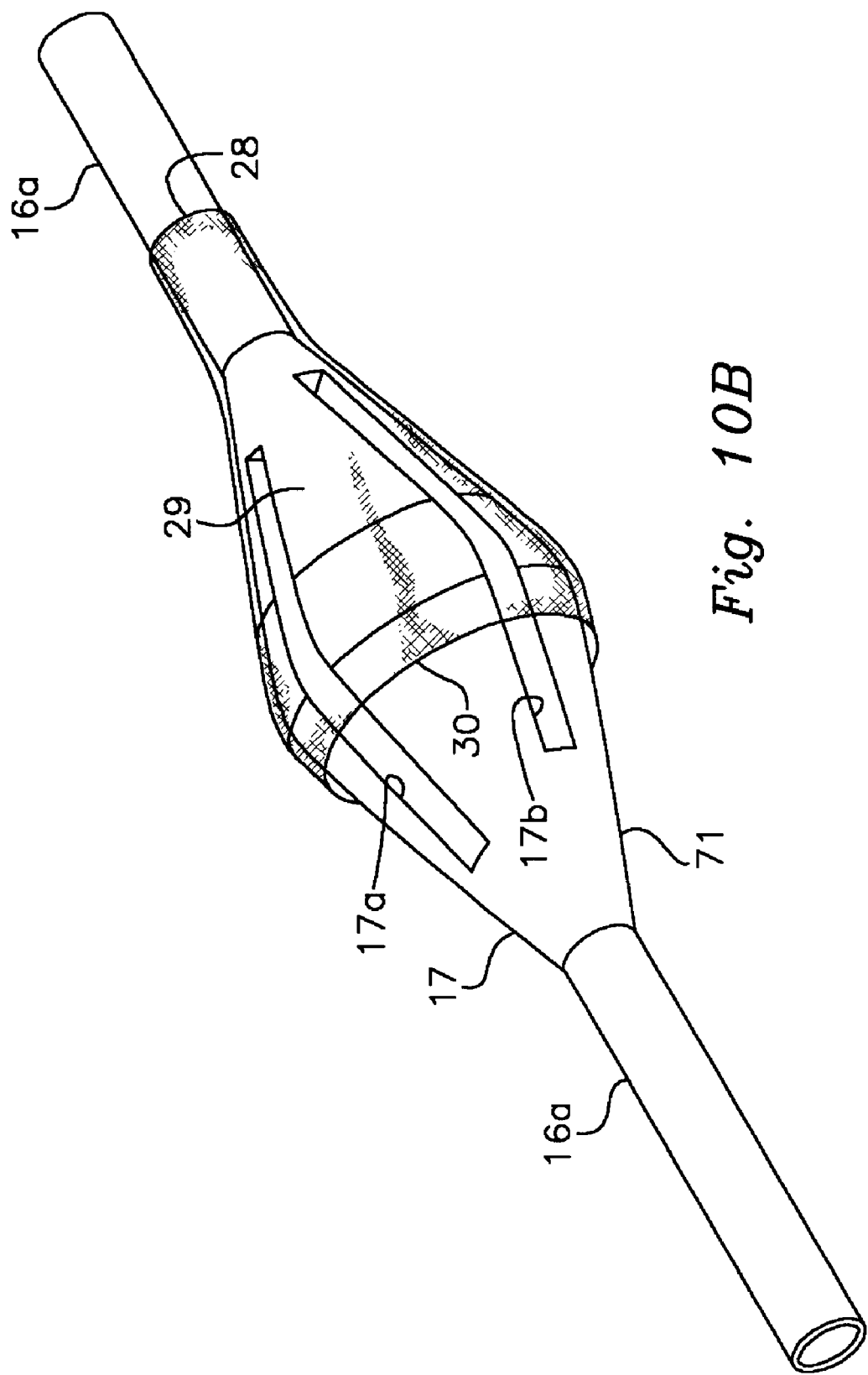
FIG. 10B is a perspective view depicting the embodiment of FIG. 10A when partially deployed.
Figure 10C:
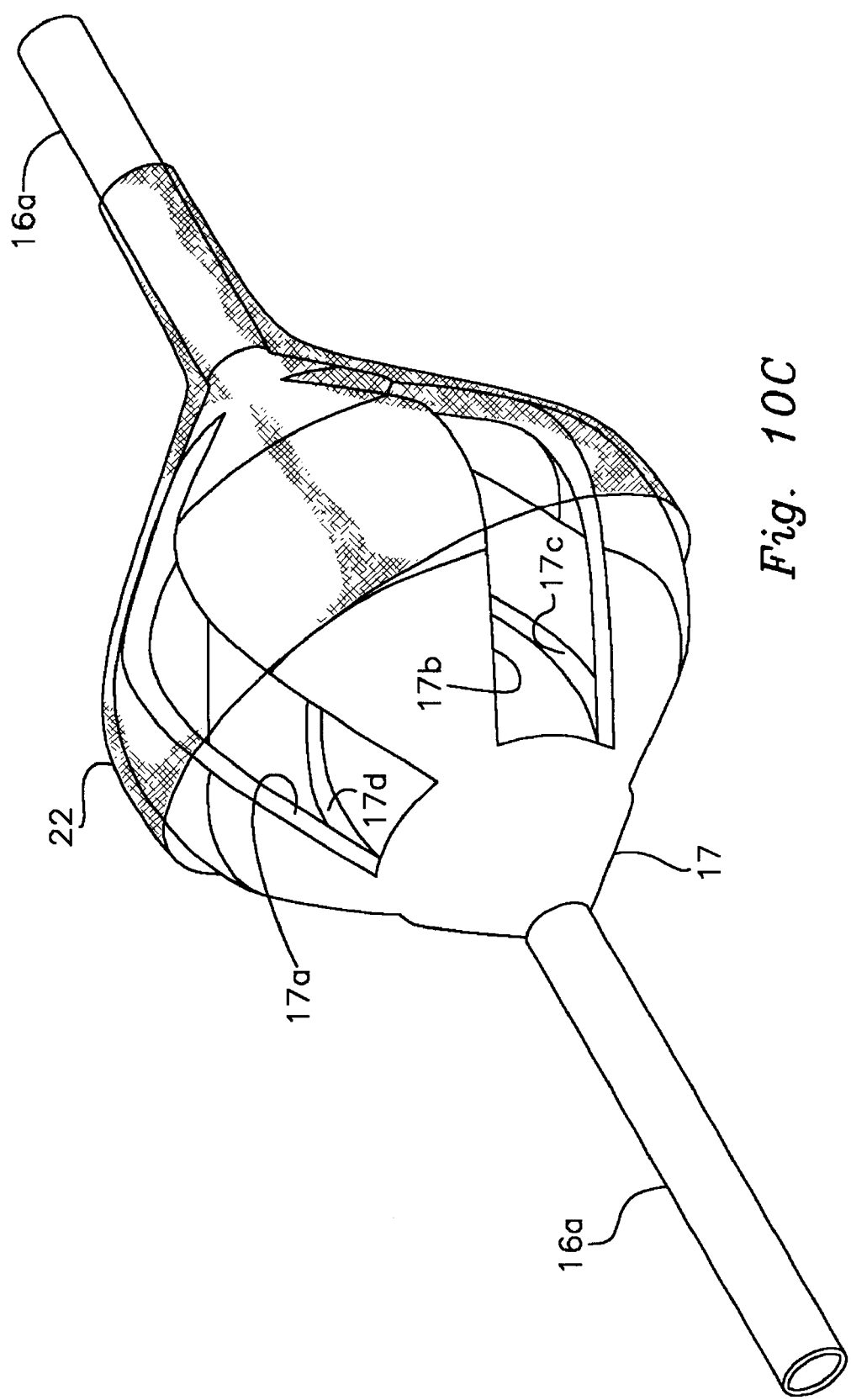
FIG. 10C is a perspective view depicting the embodiment of FIG. 10A when fully deployed.
Figure 10D:
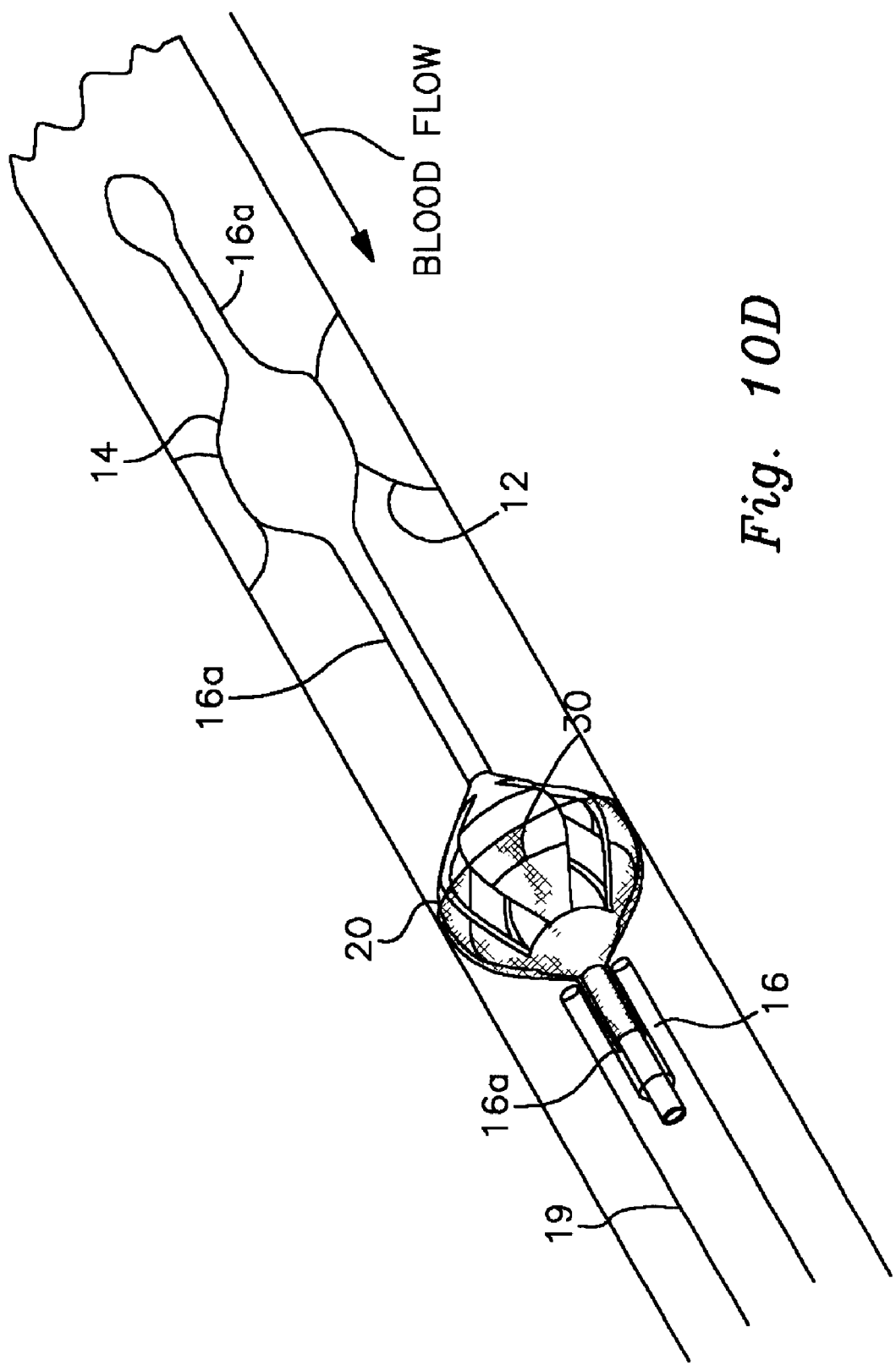
FIG. 10D is a perspective view depicting the environment of the embodiment of FIG. 10A when fully deployed in the iliac or femoral arteries.

Maximum emboli collection is achieved when the proximal, open end 30 of mesh 22 is round. It is therefore desirable to increase the number of jointed members to better approximate a circle. FIGS. 10A, 10B, 10C, and 10D disclose an embodiment where four or more jointed members are formed on an enlarged surface of an inner lumen for a balloon or stent catheter of the type having a separate inner lumen, so that opening 30 of mesh 22 is close to round; this is the second embodiment of the invention. The inner lumen is built up or enlarged as at 17, and elongate slots 17a, 17b (depicted in FIG. 10A), 17c, and 17d (not visible in FIG. 10A) are formed in said enlarged part. This not only increases the number of longitudinal slots that may be formed, it also provides jointed members having rounded profiles as is clear from the drawings. FIG. 10D depicts this embodiment when in use in arteries below the heart level where ability to capture emboli below the lesion is important. Note the substantial roundness of the open end 30 of mesh 22. This enables it to conform to the lumen of the artery it spans. This embodiment could provide a mesh structure as a middle laminate to the inner lumen 16 and the enlarged body 17.

Significantly, if the inner lumen is made of an appropriate material, such as aluminum, there is no need to provide an enlarged part, i.e., the slots can be formed in an inner lumen having no enlarged section.

Figure 11A:
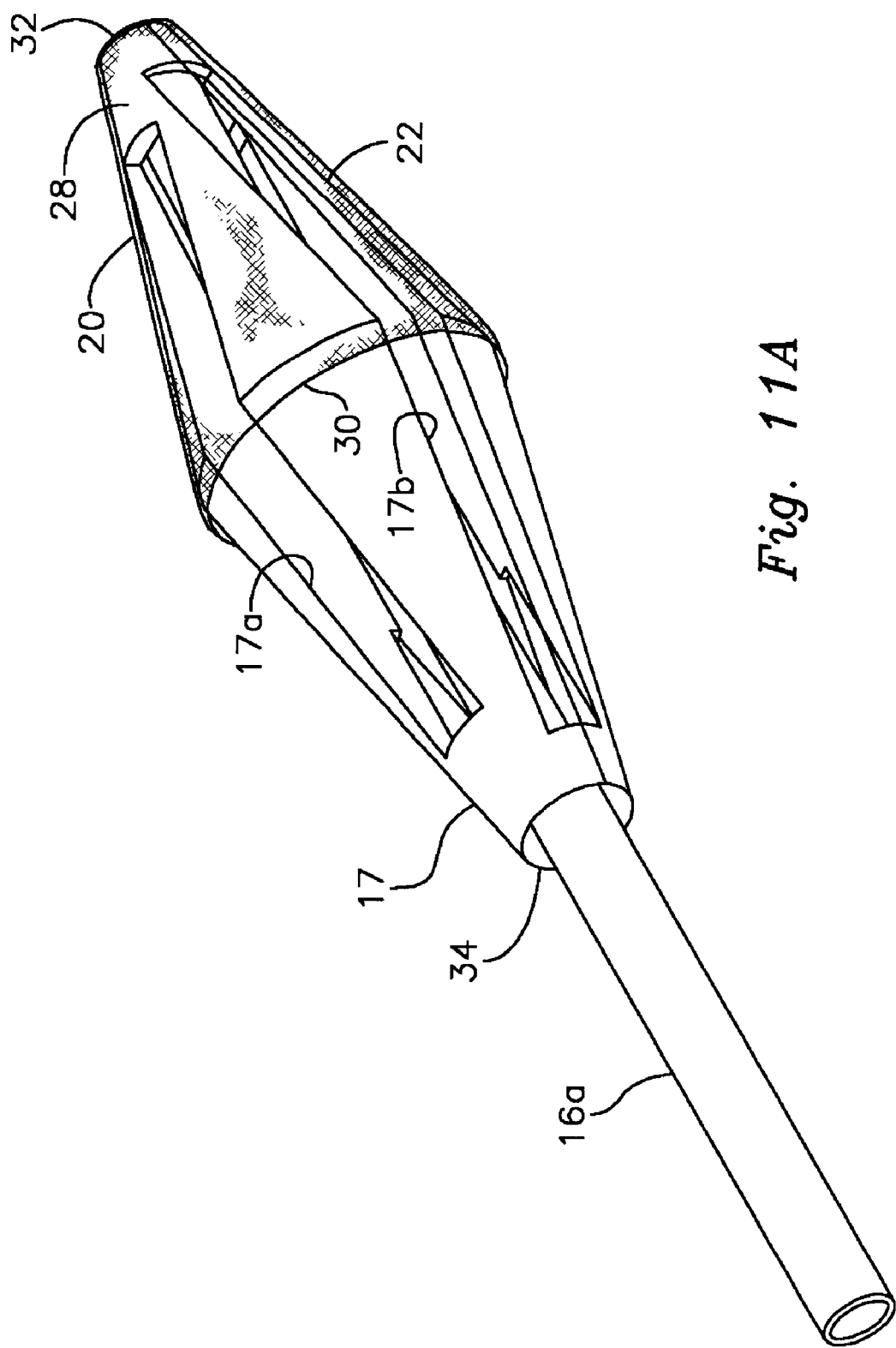
FIG. 11A is a perspective view of an embodiment similar to that of the FIG. 10A embodiment, where an inner lumen is enlarged at the distal end or tip of the catheter.
Figure 11B:
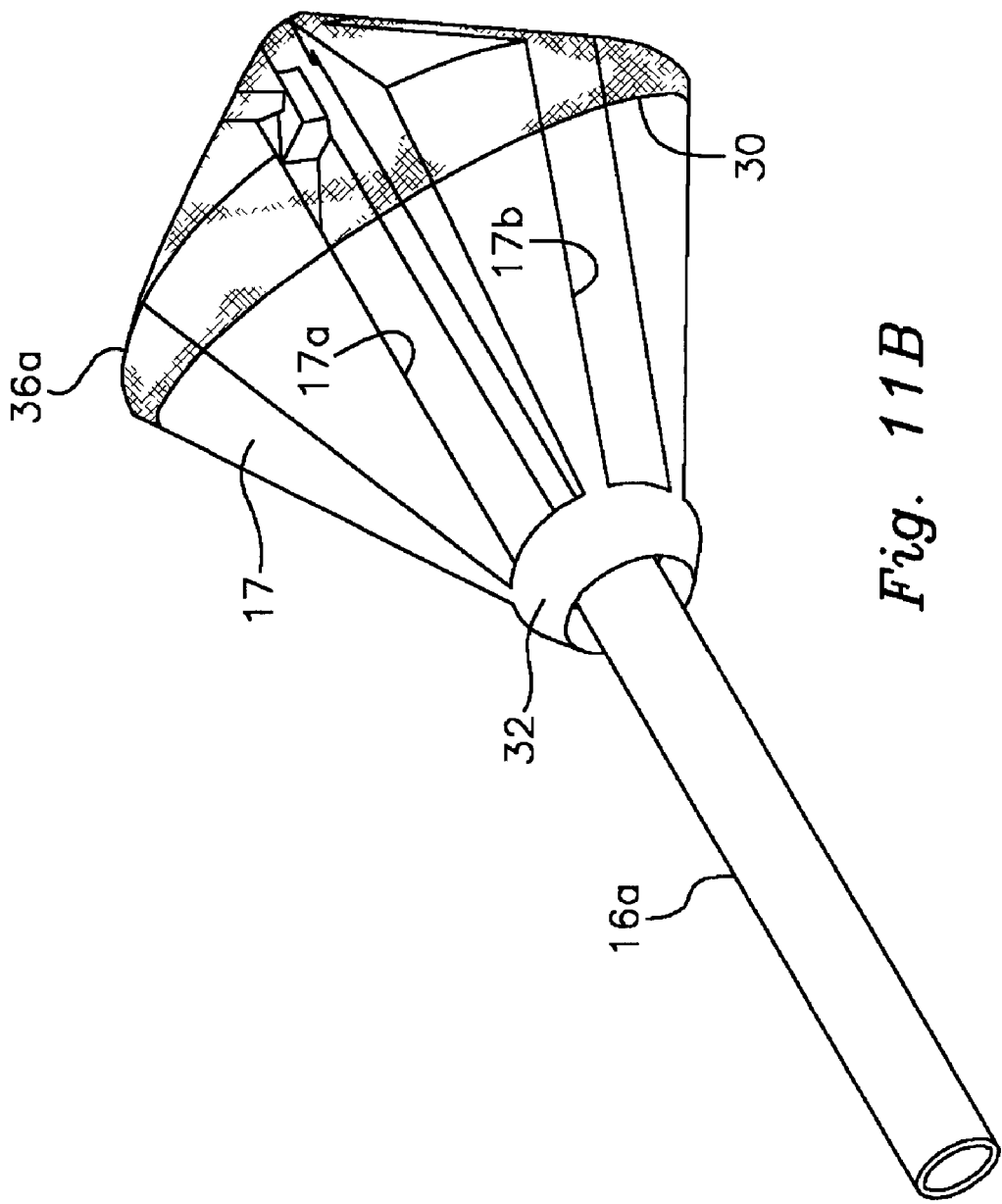
FIG. 11B is a perspective view depicting the embodiment of FIG. 11A when fully deployed.

FIGS. 11A and 11B show a variation of the embodiment of FIGS. 10A–D when the enlarged surface is molded over the distal end of an inner lumen to form the tip of the catheter assembly. FIG. 11A depicts this embodiment when frame 20 is in repose at the distal tip of the inner lumen. Each jointed member has a profile like that of an isosceles triangle so that open end 30 of mesh 22 has a larger diameter than closed end 28 thereof even before the distance between the distal and proximal joints 32, 34 is decreased. This embodiment could also provide a mesh structure as a middle laminate to the inner lumen 16 and the enlarged body 17.

Figure 12A:
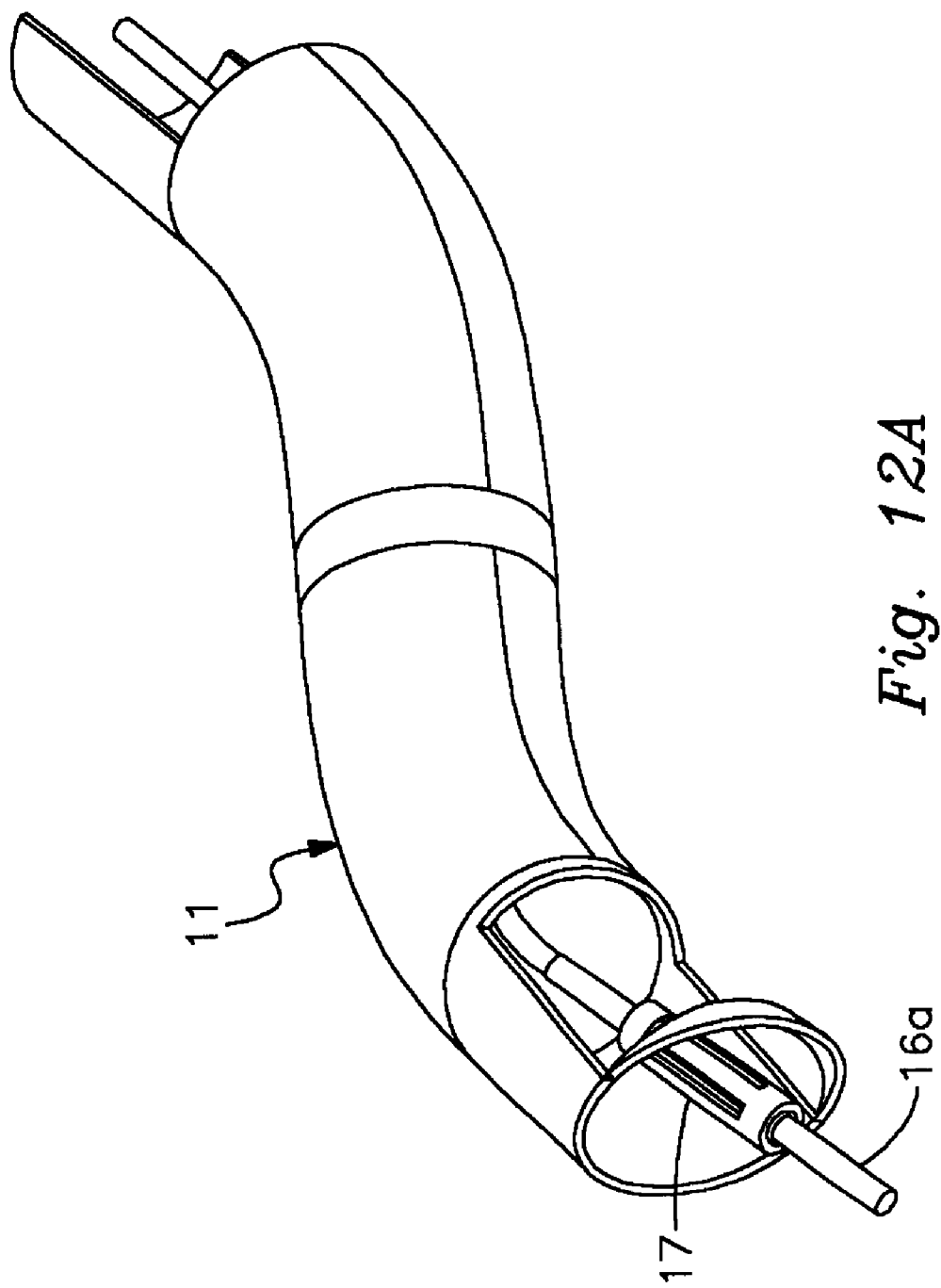
FIG. 12A is a perspective view depicting the embodiment of FIG. 10A when deployed in an artery and when in its position of repose.
Figure 12B:
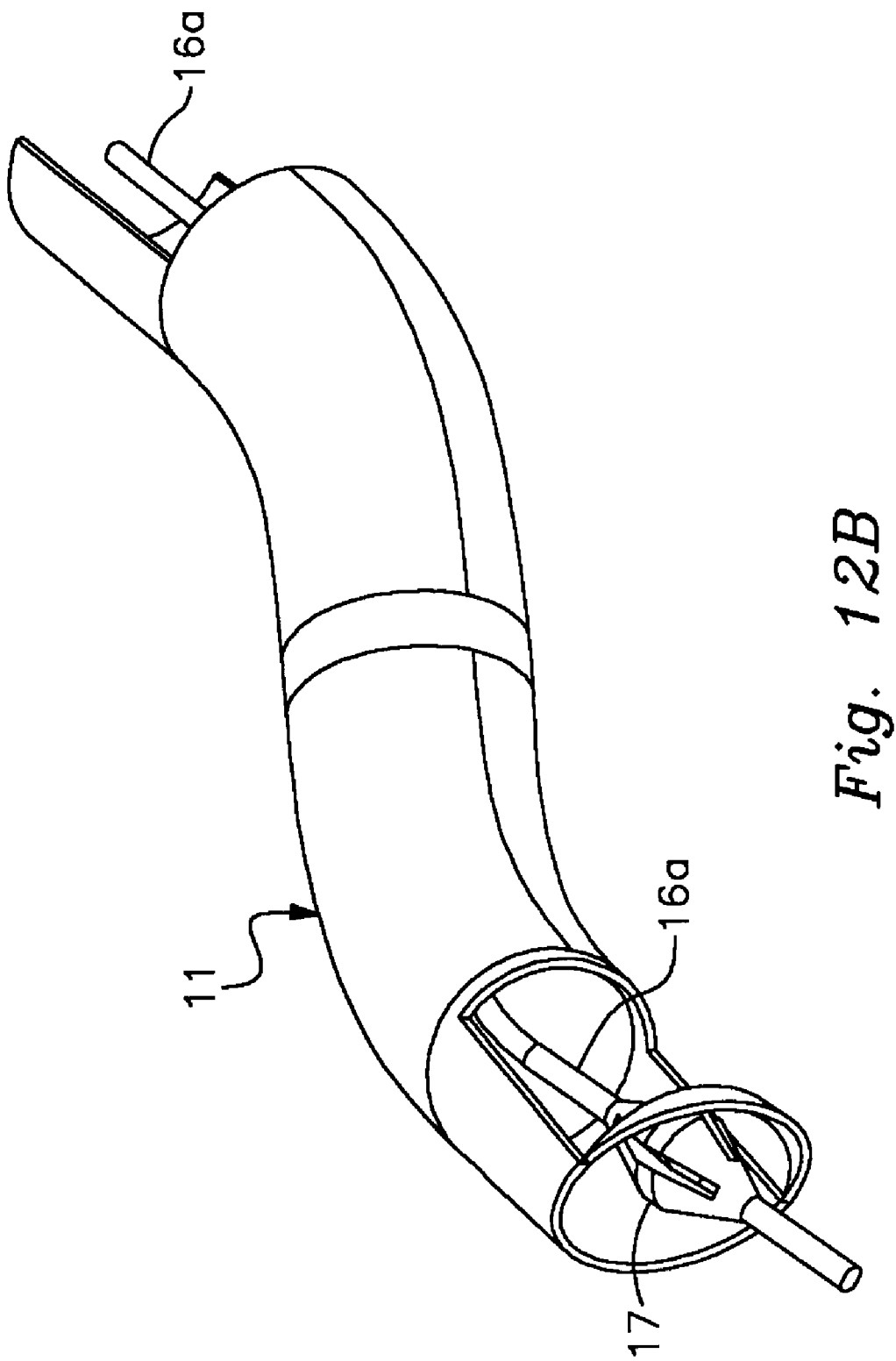
FIG. 12B is a perspective view like that of FIG. 12A, depicting said embodiment when partially deployed.
Figure 12C:
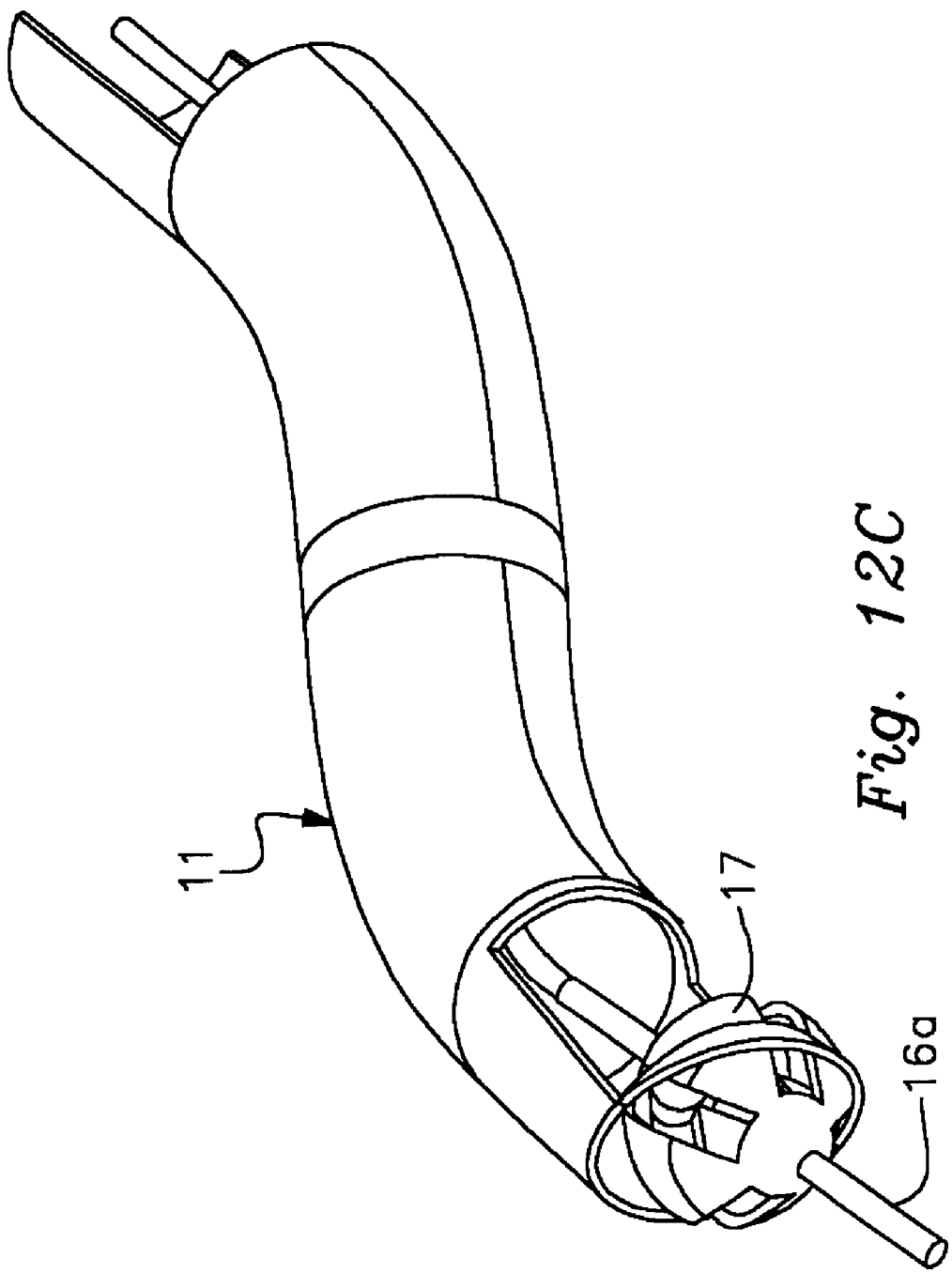
FIG. 12C is a perspective view like that of FIG. 12A, depicting said embodiment when fully deployed.

FIGS. 12A–C depict the embodiment of FIGS. 10A–D when disposed within an artery 10. FIG. 12A depicts frame 20 in its closed position. FIG. 12B depicts said frame in its partially deployed configuration, and the jointed members are fully deployed in FIG. 12C. Note in FIG. 12C how frame 20 completely spans the artery so that all emboli will be captured within mesh 22 (not depicted).

Figure 13A:
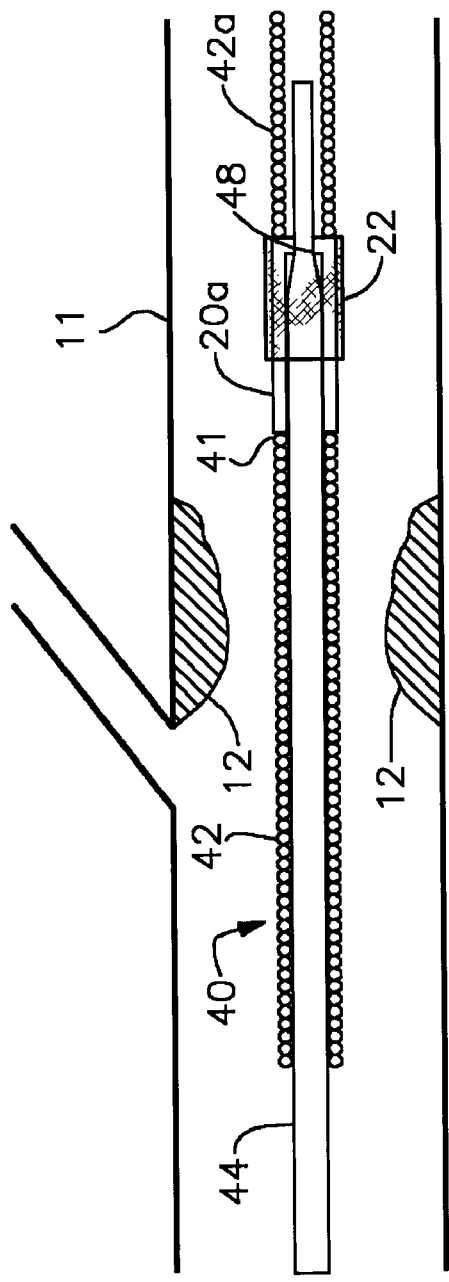
FIG. 13A is a longitudinal sectional view of an artery, depicting a third embodiment of the invention where the novel frame is formed in a guidewire, depicting the frame in its position of repose.
Figure 13B:
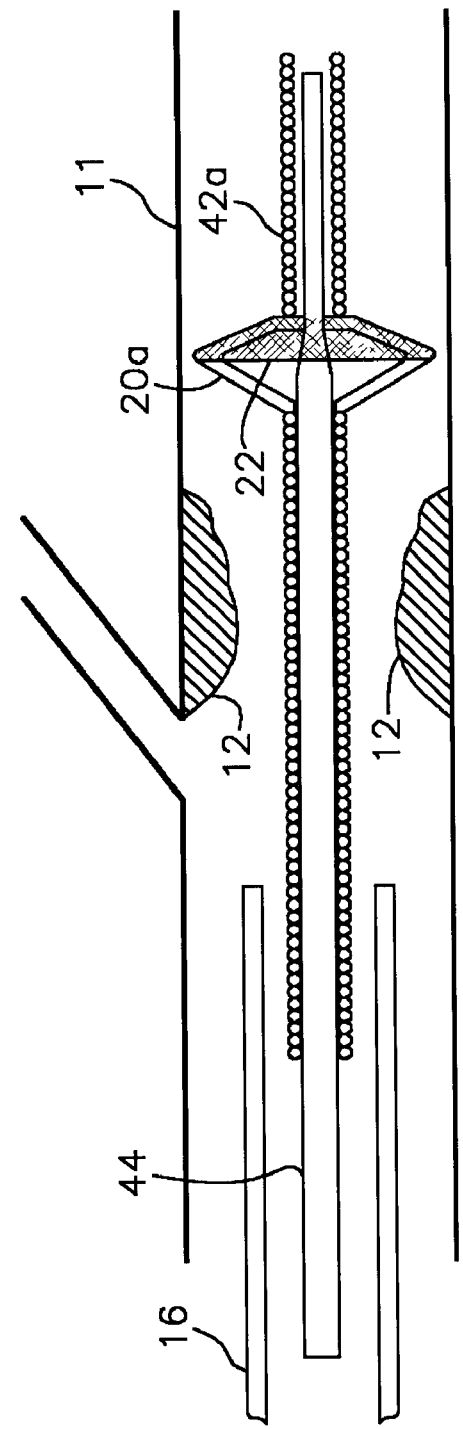
FIG. 13B is a view like that of FIG. 13A, depicting the novel frame when in its deployed configuration.

In a third embodiment of the invention, depicted in FIGS. 13A–B, a modified elongate guide wire 40 of the type having a coiled, flexible outer structure 42 that slidably receives an elongate inner rod 44 therein is used. The modification includes two additional segments brazed onto the distal end 41 of guidewire 40. The first segment, denoted 20a, is formed of a nickel-titanium alloy and includes a plurality of jointed members. The second segment, denoted 42a, is brazed onto the distal end of first segment 20a and is formed of the same material as coiled, flexible outer structure 42. Inner rod 44 is secured to the distal end of slotted segment 20a as at 48. Accordingly, axial retraction of inner rod 44 deploys the jointed members 20a as indicated in FIG. 13B and opens mesh 22 to enable emboli capture. Balloon or guide catheter 16 (FIG. 13B) may be displaced in a proximal-to-distal direction, as in the previous embodiments, to collapse the jointed members when the angioplasty procedure is over. Alternatively, the closing of the jointed members and hence of the mesh structure may be accomplished by reversing the direction of inner rod 44.

A variation of the third embodiment is depicted in FIGS. 14A and 14B, and is denoted 40a as a whole. Guidewire 40a includes an outer structure 42a made of a nickel-titanium alloy and an inner core 44a slideably received therewithin. An elongate slot 50 is formed in outer structure 42a to allow longitudinal movement of pin 52 that extends diametrically through annular bushing 54 to slidably secure said bushing 54 to said outer structure 42a. A similar bushing 56 encircles said outer structure 42a and is interconnected to bushing 54 by a plurality of jointed members, collectively denoted 58. Jointed members 58 are also preferably made of a nickel-titanium alloy. However, their deployment and closing is under the positive control of inner rod 44a as understood upon comparison of FIGS. 14A and 14B. Mesh 22 is in its position of repose in FIG. 14A and in its emboli-collecting position in FIG. 14B.

In all embodiments, mesh 22 may be impregnated with an anti-clotting compound such as Heprin® to further enhance its utility.

The novel apparatus is not limited to balloon angioplasty procedures. It has utility in connection with any procedure where blood clots are broken into smaller pieces, including any surgical procedure in which a plaque-filled vessel is clamped.

This invention represents a major breakthrough in the art of balloon angioplasty and/or stenting. Being drawn to a pioneering invention, the claims that follow are entitled, as a matter of law, to broad interpretation to protect the heart or essence of the invention from piracy.

It will thus be seen that the objects set forth above, and those made apparent from the foregoing description, are efficiently attained. Since certain changes may be made in the foregoing construction without departing from the scope of the invention, it is intended that all matters contained in the foregoing construction or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

Now that the invention has been described,
What is claimed is:

1. An apparatus for performing balloon angioplasty and stenting, comprising:

a guide wire of elongate, flexible construction;

a balloon catheter that slideably receives said guide wire;

a guide catheter that slideably receives said balloon catheter;

a plurality of jointed members formed in said balloon catheter near a distal end thereof;

said jointed members having a position of repose where they are substantially flush with said balloon catheter;

each joint member of said plurality of joint members having a proximal joint, a distal joint that is longitudinally spaced apart from said proximal joint, and a middle joint that is substantially half-way between said proximal and distal joints;

said jointed members having a deployed configuration where each middle joint is displaced radially outwardly, with respect to a longitudinal axis of said balloon catheter, when each distal joint is displaced toward its associated proximal joint;

first positive displacement means for selectively displacing each of said distal joints toward their respective proximal joints;

said first positive displacement means including an enlargement means formed on a distal end of said guide wire, said enlargement means having a breadth greater than an inner diameter of said balloon catheter so that displacement of said guide wire in a distal-to-proximal direction causes each of said middle joints to displace radially outwardly with respect to said longitudinal axis of said balloon catheter;

second positive displacement means for selectively displacing each of said distal joints away from their respective proximal joints;

said second positive displacement means including said guide catheter, said guide catheter collapsing said jointed members and returning them to said position of repose when said guide catheter is displaced in a proximal-to-distal direction;

a mesh structure of flexible construction disposed in ensleeving relation to said balloon catheter;

a first, distal end of said mesh structure being secured to said balloon catheter at a preselected location just slightly distal of said jointed members;

a second, proximal end of said mesh structure extending to a preselected point just slightly proximal of said middle joints of said jointed members;

said second, proximal end of said mesh structure being enlarged in diameter when said middle joints are displaced radially outwardly;

said mesh structure allowing blood to flow therethrough;

said mesh structure capturing and retaining emboli from a balloon angioplasty procedure when said middle joints are displaced radially outwardly; and said mesh structure returning to a position of repose when said middle joints are displaced radially inwardly.

2. The apparatus of claim 1, wherein said first, distal end of said mesh structure is woven with a relatively loose mesh structure.

3. The apparatus of claim 2, wherein said second, proximal end of said mesh structure is woven with a relatively tight mesh structure.

4. The apparatus of claim 3, wherein a transition between said relatively loose mesh structure and said relatively tight mesh structure occurs about mid-length between said first, distal end and said second, proximal end of said mesh structure.

5. The apparatus of claim 1, wherein said first, distal end of said mesh structure is adhered to said balloon catheter at said preselected position distal of said jointed members.

* * * * *